US009127082B2

(12) United States Patent
Saarma et al.

(10) Patent No.: US 9,127,082 B2
(45) Date of Patent: Sep. 8, 2015

(54) MANF2 FOR TREATMENT OF PARKINSON'S DISEASE

(75) Inventors: Mart Saarma, Helsinki (FI); Juha Lauren, New Haven, CT (US); Paivi Lindholm, Vantaa (FI); Tonis Timmusk, Tallinn (EE); Raimo Tuominen, Vantaa (FI)

(73) Assignee: HERANTIS PHARMA PLC., Helsinki (FI)

(*) Notice: Subject to any disclaimer, the term of this patent is extended or adjusted under 35 U.S.C. 154(b) by 1293 days.

(21) Appl. No.: 12/037,535

(22) Filed: Feb. 26, 2008

(65) Prior Publication Data

US 2008/0269154 A1 Oct. 30, 2008

Related U.S. Application Data

(60) Division of application No. 11/330,359, filed on Jan. 12, 2006, now abandoned, which is a continuation-in-part of application No. 10/648,361, filed on Aug. 27, 2003, now Pat. No. 7,452,969, said application No. 11/330,359 is a continuation of application No. PCT/FI2005/050461, filed on Dec. 14, 2005.

(60) Provisional application No. 60/406,927, filed on Aug. 30, 2002.

(51) Int. Cl.
*A61K 48/00* (2006.01)
*A61P 25/16* (2006.01)
*C12N 15/86* (2006.01)
*C07K 14/475* (2006.01)
*A61K 38/00* (2006.01)

(52) U.S. Cl.
CPC ............ *C07K 14/475* (2013.01); *A01K 2217/05* (2013.01); *A01K 2217/075* (2013.01); *A01K 2227/105* (2013.01); *A01K 2267/0356* (2013.01); *A61K 38/00* (2013.01)

(58) Field of Classification Search
None
See application file for complete search history.

(56) References Cited

U.S. PATENT DOCUMENTS

| 6,015,572 | A | * | 1/2000 | Lin et al. | 424/424 |
| 6,783,969 | B1 | * | 8/2004 | Tang et al. | 435/219 |
| 7,452,969 | B2 | | 11/2008 | Saarma et al. | |
| 2002/0182198 | A1 | | 12/2002 | Commissiong et al. | |
| 2004/0053250 | A1 | | 3/2004 | Tang et al. | |
| 2006/0057582 | A1 | | 3/2006 | Rosen et al. | |
| 2006/0084619 | A1 | | 4/2006 | Saarma et al. | |
| 2006/0195915 | A1 | | 8/2006 | Saarma et al. | |

FOREIGN PATENT DOCUMENTS

| EP | 1 033 401 A2 | 9/2000 |
| WO | WO-01/19851 A2 | 3/2001 |
| WO | WO-01/55317 A2 | 8/2001 |
| WO | WO-01/55320 A2 | 8/2001 |
| WO | WO-01/70174 A2 | 9/2001 |
| WO | WO-02/068638 A1 | 9/2002 |
| WO | WO-02/070539 A2 | 9/2002 |
| WO | WO-02/074956 A2 | 9/2002 |
| WO | WO-02/079246 A2 | 10/2002 |
| WO | WO 02079246 * | 10/2002 |
| WO | WO-02/098902 A2 | 12/2002 |

OTHER PUBLICATIONS

Kahle et al, The emerging utility of animal models of chronic neurodegenerative disease, Emerging Therapeutic Targets (2001) 5(1):125-132.*
Lazic and Barker, Cell-based therapies for disorders of the CNS, Expert Opin. Ther. Patents (2005) 15(10): 1361-1376.*
Verma and Somia, Gene Therapy—promises,problems and prospects, Nature, 1997, vol. 389, pp. 239-242.*
Russell, Replicating Vectors for Gene Therapy of Cancer: Risks, Limitations and Prospects, European j Cancer, 1994. vol. 30A(8), pp. 1165-1171.*
Opalinska et al, Nucleic-Acid Therapeutics: Basic Principles and Recent Applications, Nature Reviews, 2002, vol. 1, p. 503-514.*
Richardson and Burns, Mouse Models of Alzheimer's Disease: A Quest for Plaques and Tangles, ILAT Journal, 2002, vol. 43 (2), p. 89-99.*
Back et al, Gene therapy with AAV2-CDNF provides functional benefits in a rat model of Parkinson's disease.*
Bibel et al., Genes and Development, 14:2919-2937, 2000.
Peaire et al., Journal of Neuroscience Methods, 124, 61-74 (2003).
Airaksinen et al., Molecular and Cellular Neuroscience, 13, 313-325 (1999).
Airaksinen et al., Nature Reviews Neuroscience, vol. 3, 383-394, May 2002.
Shridhar et al., Oncogene, 12, 1931-1939 (1996).
Shridhar et al., Oncogene, 14, 2213-2216 (1997).
Petrova et al., Journal of Molecular Neuroscience, vol. 20, 173-187 (2003).
Okazaki et al., Nature, vol. 420, 563-573, Dec. 2002 (with supplementary information).
Genbank Accession No. AX573504: WO 02/079246 A 8 Oct. 10, 2002.
Genbank Accession No. BC037872: R. Strausberg, NIH-MGC Project, National Institutes of Heath, Mammalian Gene Collection (MGC), Submitted (Sep. 16, 2002).
Genbank Accession No. A1807908: NCI-CGRP, National Cancer Institute, Cancer Genome Anatomy Project, Tumor Gene Index, Unpublished (1997).

(Continued)

*Primary Examiner* — Maria Marvich
(74) *Attorney, Agent, or Firm* — Birch, Stewart, Kolasch & Birch, LLP

(57) ABSTRACT

The present invention discloses a novel neurotrophic factor protein, MANF2 and a genetic sequence encoding the same. The molecule will be useful in the development of a range of therapeutics and diagnostics useful in the treatment, prophylaxis and/or diagnosis of MANF2 dependent conditions. The molecule of the present invention is also a useful effector of primary and central neurons, especially dopaminergic neurons at the central nervous system and growth factor genes.

2 Claims, 17 Drawing Sheets

(56) References Cited

OTHER PUBLICATIONS

Genbank Accession No. BI464979: NIH-MGC, National Institutes of Health, Mammalian Gene Collection (MGC), Unpublished (1999).
Genbank Accession No. BG742840: NIH-MGC, National Institutes of Health, Mammalian Gene Collection (MGC) Unpublished (1999).
Genbank Accession No. F31353: G. Lanfranchi at al., Genome Res. 6 (1), 35-42 (1996).
Genbank Accession No. BG742772: NIH-MGC, National Institutes of Health, Mammalian Gene Collection (MGC), Unpublished (1999).
Genbank Accession No. AA018863: L. Hillier et al., Genome Res. 6 (9), 807-828 (1996).
Genbank Accession No. AV657190: X Xu et al., Proc. Natl. Acad. Sci. USA 98 (26), 15089-15094 (2001).
Genbank Accession No. BD030478: J. B. D. M. Edwards et al., JP 2001-269182-A 6724 Oct. 2, 2001.
Genbank Accession No. AK034009: P. Carninci et al., Meth. Enzymol. 303, 19-44 (1999) P. Carninci et al., Genome Res. 10 (10), 1617-1630 (2000) K. Shibata et al., Genome Res. 10 (11), 1757-1771 (2000) J. Kawai et al., Nature 409 (6821), 685-690 (2001) The Fantom Consortium and the Riken Genome Exploration Research Group Phase I & II Team, Nature 420, 563-573 (2002) J. Adachi et al., The Institute for Physical and Chemical Research (RIKEN), Submitted (Jul. 16, 2001).
Genbank Accession No. BB625884: T. Arakawa et al., Laboratory for Genome Exploration Research Group, RIKEN Genomic Sciences Center, Unpublished (2001).
Genbank Accession No. BI964826: D. Melton et al., Endocrine Pancreas Consortium, Harvard University, Howard Hughes Medical Center, Unpublished (2000).
Genbank Accession No. AX573503: L. Bougueleret et al., WO 02/079246-A 7 Oct. 10, 2002.
Genbank Accession No. AC069544: D. R. Smith, Genome Therapeutics Corp. Submitted (Jun. 2, 2000) D. R. Smith, Genome Therapeutics Corp. Submitted (Dec. 21, 2001) D. R. Smith, Genome Therapeutics Corp. Submitted (Apr. 25, 2002).
Genbank Accession No. AQ412924: S. Zhao et al., Department of Eukaryotic Genomics, The Institute for Genomic Research, Unpublished (1997).
Genbank Accession No. AX573508: L. Bougueleret, WO 02/079246-A 12 Oct. 10, 2002.
Genbank Accession No. AZ537498: G. Henkel; Aurora Biosciences Corp, Unpublished (2000).
Genbank Accession No. AI214900: NCI-CGAP, National Cancer Institute, Cancer Genome Anatomy Project (CGAP), Tumor Gene Index, Unpublished (1997).
Genbank Accession No. B0213461: J. J. Harrington, Nat. Biotechnol. 19 (5), 440-445 (2001).
Genbank Accession No. BI963176: D. Melton, Endocrine Pancreas Consortium, Harvard University, Howard Hughes Medical Institute, Unpublished (2000).
Genbank Accession No. AA725810: NCI-CGAP, National Cancer Institute, Cancer Genome Anatomy Project (CGAP), Tumor Gene Index, Unpublished (1997).
Genbank Accession No. AX573502: L. Bougueleret at al., WO 02/079246-A 6 Oct. 10, 2002.
Genbank Accession No. AX573525: L. Bougueleret et al., WO 02/079246-A 29 Oct. 10, 2002.
Genbank Accession No. AX573507: L. Bougueleret et al., WO 02/079246-A 11 Oct. 10, 2002.
Genbank Accession No. AA018896: L. Hillier et al., The WashU-Merck EST Project, Washington University School of Medicine, Unpublished (1995).
Genbank Accession No. BF150043: NCI-CGAP, National Cancer Institute, Cancer Genome Anatomy Project (CGAP), Tumor Gene Index, Unpublished (1997).
Genbank Accession No. AA885943: NCI-CGAP, National Cancer Institute, Cancer Genome Anatomy Project (CGAP), Tumor Gene Index, Unpublished (1997).
Genbank Accession No. AX573506: L. Bougueleret et al., WO 02/079246-A 10 Oct. 10, 2002.
Genbank Accession No. AX573505: L. Bougueleret et al., WO 02/079246-A 9 Oct. 10, 2002.
Genbank Accession No. CB785684: Amgen EST Program, Amgen, Inc., Unpublished (2003).
Genbank Accession No. AQ458921: G. G. Mahairas et al., Proc. Natl. Acad. Sci. USA 96 (17) 9739-9744 (1999).
Genbank Accession No. AAH07282: R. Strausberg, National Institutes of Health, Mammalian Gene Collection (MGC), Submitted (May 1, 2001).
Genbank Accession No. AAB08753: V. Shridhar et al., Oncogene 12 (9), 1931-1939 (1996).
Smith and Zhang, The challenges of genome sequence annotation or "The devil is in the details", Nature Biotechnology, Nov. 1997, vol. 15, pp. 1222-1223.
Tseng and Liang, Evolutionary model for predicting protein function by matching local surfaces: a Bayesian Monte Carlo approach, poster abstract downloaded Jun. 9, 2005.
Tertiary structures—Biology Pages, downloaded Oct. 14, 2005.
Smith et al., Surface point mutations that significantly alter the structure and stability of a protein's denatured state, Protein Science, 1996, vol. 5, pp. 2009-2019.
Torchilin, V.P., et al, "Peptide and protein drug delivery to and into tumors: challenges and solutions," DDT, Mar. 2003, vol. 8, No. 6, pp. 259-266.
USPTO Office Action dated Dec. 22, 2011 for U.S. Appl. No. 13/088,233.
Deumens et al., "Modeling Parkinson's Disease in Rats: An Evaluation of 6-OHDA Lesions of the Nigrostriatal Pathway," Experimental Neurology, vol. 175, 2002, pp. 303-317.
Lindholm et al., "Novel group of evolutionary conserved neurotrophic factors promote the survival of mouse dopaminergic neurons," European Life Scientist Organization (ELSO), Abstract No. 328, Sep. 3-6, 2005.
Mahairas et al., "Sequence-Tagged Connectors: A Sequence Approach to Mapping and Scanning the Human Genome", High Throughput Sequencing Center, Created Apr. 21, 1999.
Patel et al., "GDNF delivery for Parkinson's disease," Acta Neurochir. Suppl., vol. 97, No. 2, 2007, pp. 135-154.
Rosen et al., "DNA (human clone HSCPT22 187-amino acid secretory protein cDNA plus flanks)", STN Database CAS Registry, Database Accession No. 455961-28-1, Sep. 27, 2002
Rosen et al., "DNA (human clone HSCPT22 187-amino acid secretory protein cDNA plus flanks)", STN Database CAS Registry, Database Accession No. 455962-11-5, Sep. 27, 2002.
Rosen et al., "Human secreted protein of the invention SEQ ID No. 203", GENESEQ Database Accession No. ADG79397, Mar. 11, 2004.
Rosen et al., "Human secreted protein of the invention SEQ ID No. 286", GENESEQ Database Accession No. ADG79480, Mar. 11, 2004.
Tang et al., "DNA (human clone WO2004087874-SEQID-719 protein cDNA contig)", STN Database CAS Registry, Database Accession No. 766439-79-6, Oct. 20, 2004.
Tang et al., "Protein factor discovery related human contig polypeptide, SEQ ID No. 1059", GENESEQ Database Accession No. ADS98795, Dec. 30, 2004.
Torchilin et al, "Peptide and protein drug delivery to and into tumors: challenges and solutions," DDT, vol. 8, No. 6, Mar. 2003, pp. 259-266.
Zhao et al., "Use of BAC End Sequences from Library RPCI-11 for Sequence-Ready Map Building", Genbank Accession No. AQ412924.1, Created Mar. 23, 1999.

\* cited by examiner

CONSTRUCTION OF AAV2 –CDNF (MANF2)
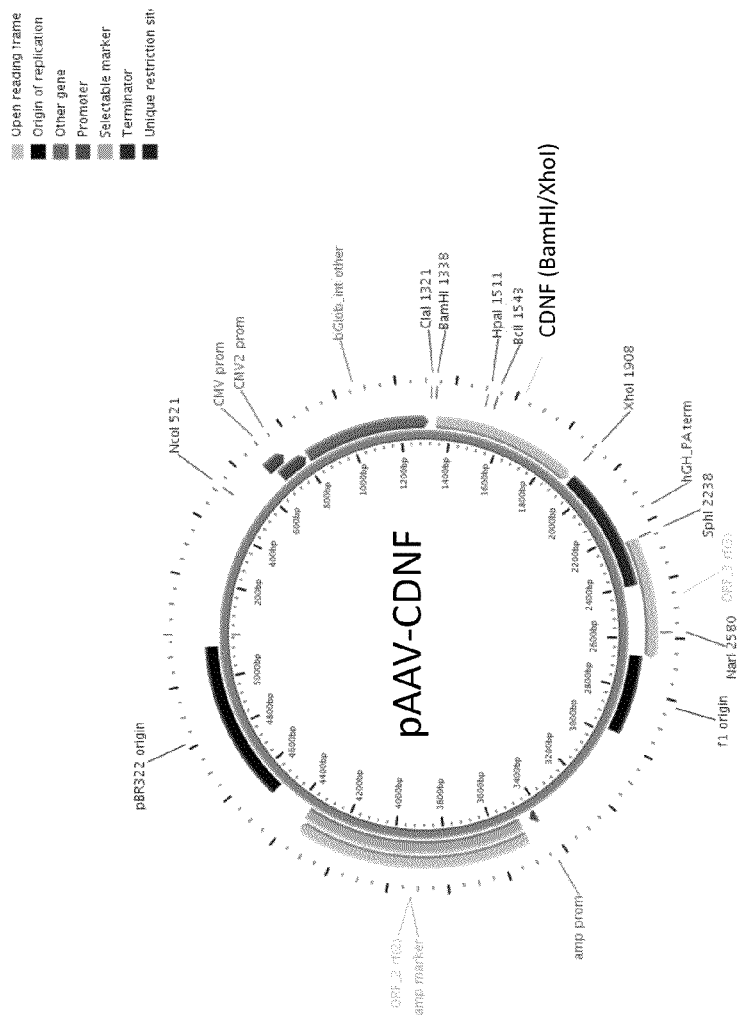
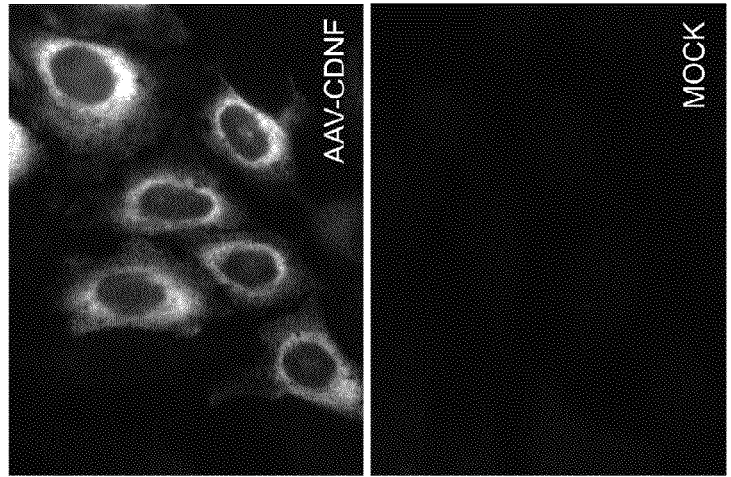
Fig. 1. The open reading frame of CDNF (MANF2) was cloned into the pAAV-MCS vector. AAV-CDNF particles were produced by co-transfecting pAAV-CDNF with two helper plasmids in HEK293 cells. Expression of CDNF from these AAV particles were tested in HeLa cells by staining the cells with anti-CDNF.

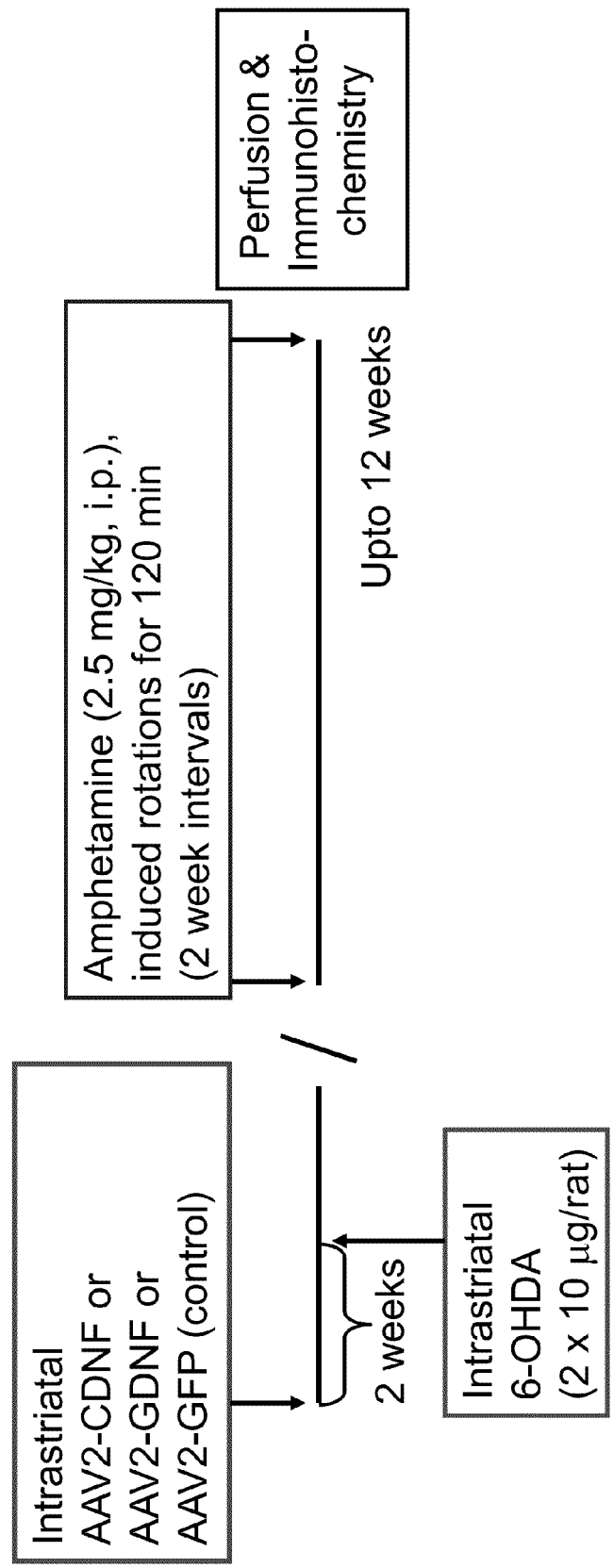
Fig. 2. Experimental plan for AAV2-CDNF

Fig. 3. AAV2-CDNF gene therapy in the 6-OHDA partial lesion model in rats
(1) AAV2-CDNF gene therapy, one injection (protection)
(2) Rats received 6-OHDA in two locations in Striatum
(1) AAV2-CDNF
AAV2-GDNF
AAV2-GFP
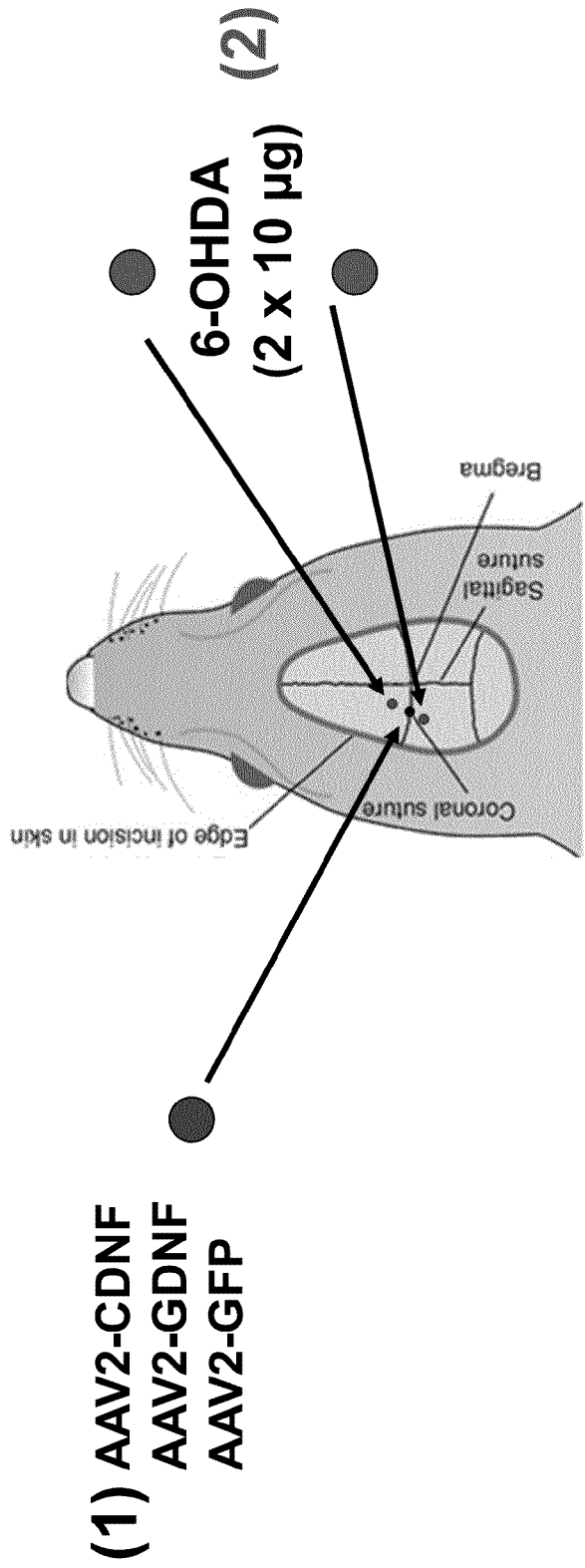

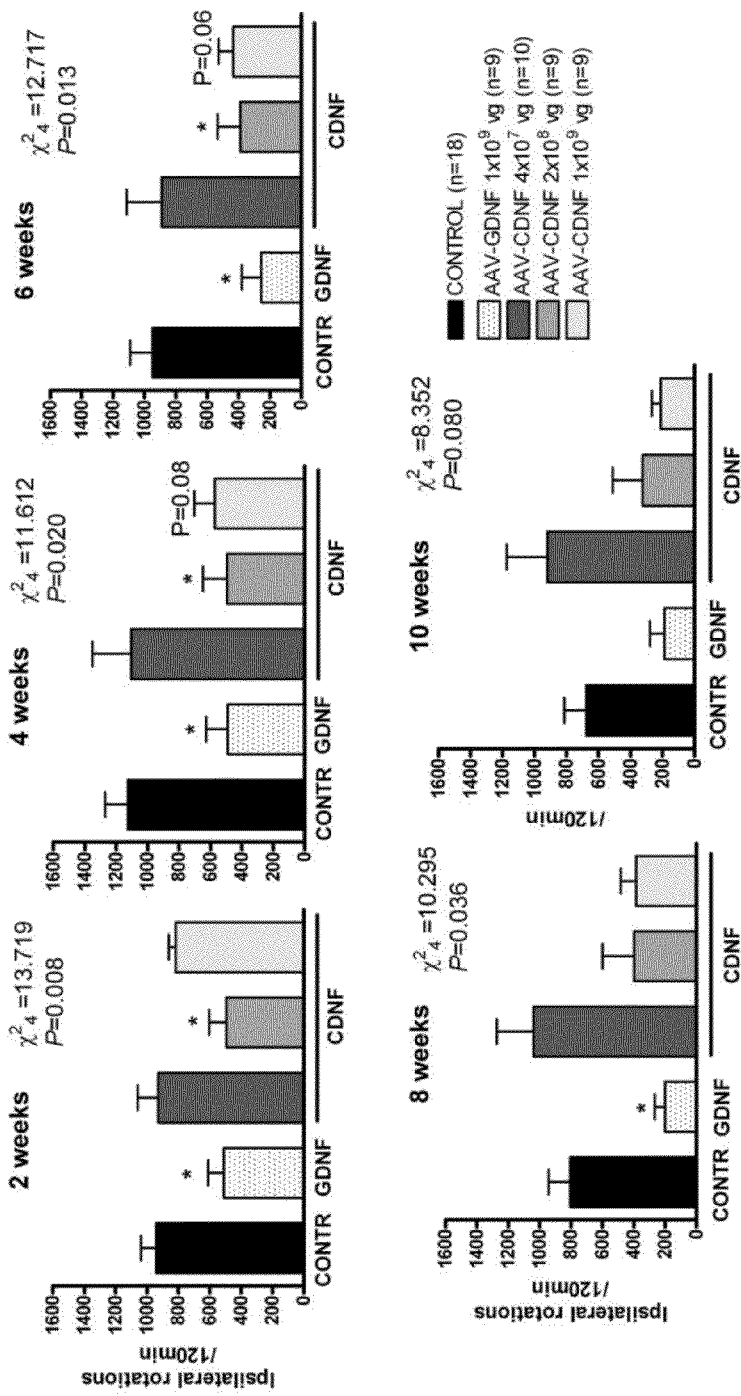
Fig. 4. The effect of AAV2-CDNF gene therapy on amphetamine-induced rotational behaviour Figure 5
A
1 2 3 4 5 6 7 8 9 10 11 12 13 14
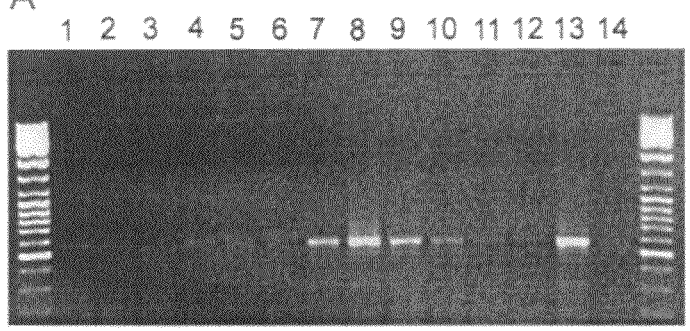
B
1 2 3 4 5 6 7 8 9 10 11 12 13
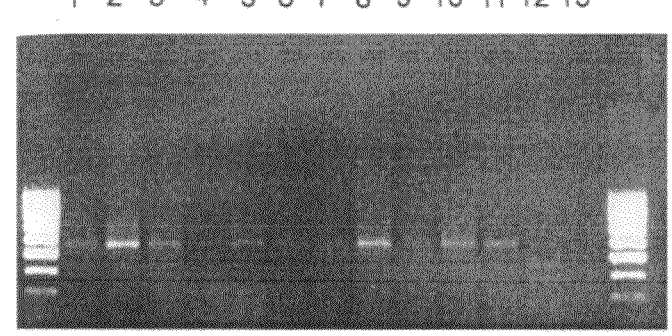
C
1 2 3 4 5 6 7 8 9 10 11
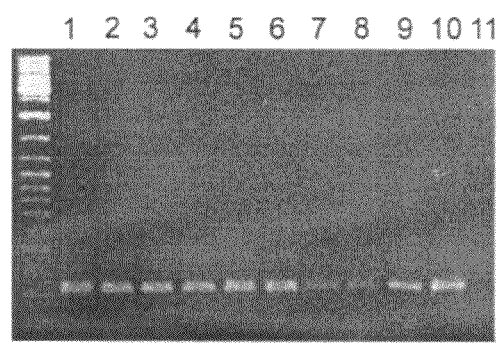

Figure 7

Seq ID NO 1:

>*Homo sapiens* MANF2 cDNA atgtggtgcgcgagcccagttgctgtggtggccttttgcgccgggcttttggtctctcacccggtgctgacgcagggccaggaggc cgggggggcggccaggggccgactgtgaagtatgtaaagaattcttgaaccgattctacaagtcactgatagacagaggagttaac ttttcgctggacactatagagaaagaattgatcagttttgcttggacaccaaaggaaaagaaaaccgcctgtgctattatctaggag ccacaaaagacgcagccacaaagatcctaagtgaagtcactcgcccaatgagtgtgcatatgcctgcaatgaagatttgtgagaa gctgaagaagttggatagccagatctgtgagctgaaatatgaaaaacactggacttggcatcagttgacctgcggaagatgaga gtggcagagctgaagcagatcctgcatagctgggggaggagtgcagggcctgtgcagaaaaaactgactatgtgaatctcattc aagagctggcccccaagtatgcagcgacacaccccaaaacagagctctga Seq ID NO 2:

>*Homo sapiens* MANF2 protein

MWCASPVAVVAFCAGLLVSHPVLTQGQEAGGRPGADCEVCKEFLNRFYKSLIDR
GVNFSLDTIEKELISFCLDTKGKENRLCYYLGATKDAATKILSEVTRPMSVHMPAM
KICEKLKKLDSQICELKYEKTLDLASVDLRKMRVAELKQILHSWGEECRACAEKT
DYVNLIQELAPKYAATHPKTEL

Seq ID NO 3:

>*Mus musculus* MANF2 cDNA atgcggtgcatcagtccaactgctctggtgaccttttgcgccgggttttgtatctcgaaccctgtgctggcgcagggcctggaggcc ggtgtggggccgagggctgactgtgaagtatgtaaagaattcttagaccgattctacaactccctgctaagcagaggcatagactt tctgcggacaccatagagaaagagctgctcaacttttgctcagatgccaaaggaaaagaaaaccgcctgtgctattatctgggggc caccacagatgcagccaccaagatcctaggagaagtcactcgtcccatgagtgtacacataccctgccgtgaagatttgtgagaag ctaaagaagatggacagccagatctgtgagctgaaatacgggaagaagctggacttggcgtcggtggacctgtggaagatgaga gtggcagagctaaagcagatccttcagagatgggggaagagtgcagggcatgtgcggagaaaagtgactacgtgaacctcatt agagagctggccccccaaatatgtagagatataccccaaacggagctctga Seq ID NO 4:

>*Mus musculus* MANF2 protein

MRCISPTALVTFCAGFCISNPVLAQGLEAGVGPRADCEVCKEFLDRFYNSLLSRGI
DFSADTIEKELLNFCSDAKGKENRLCYYLGATTDAATKILGEVTRPMSVHIPAVKI
CEKLKKMDSQICELKYGKKLDLASVDLWKMRVAELKQILQRWGEECRACAEKS
DYVNLIRELAPKYVEIYPQTEL

A
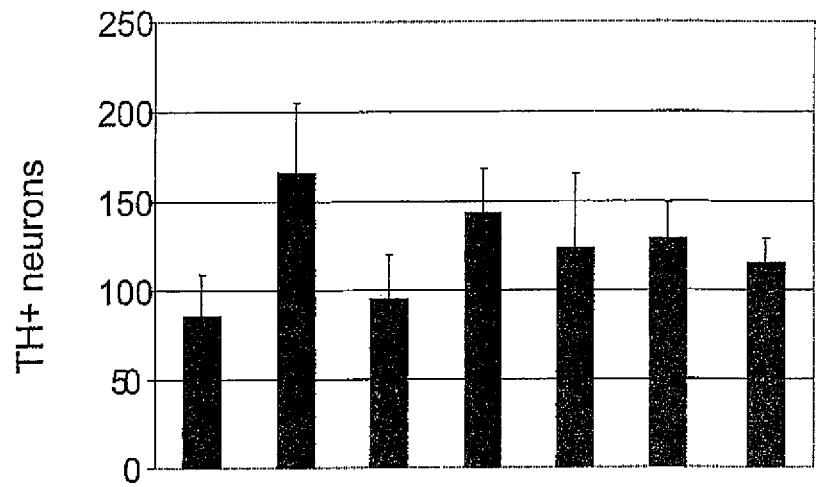
B
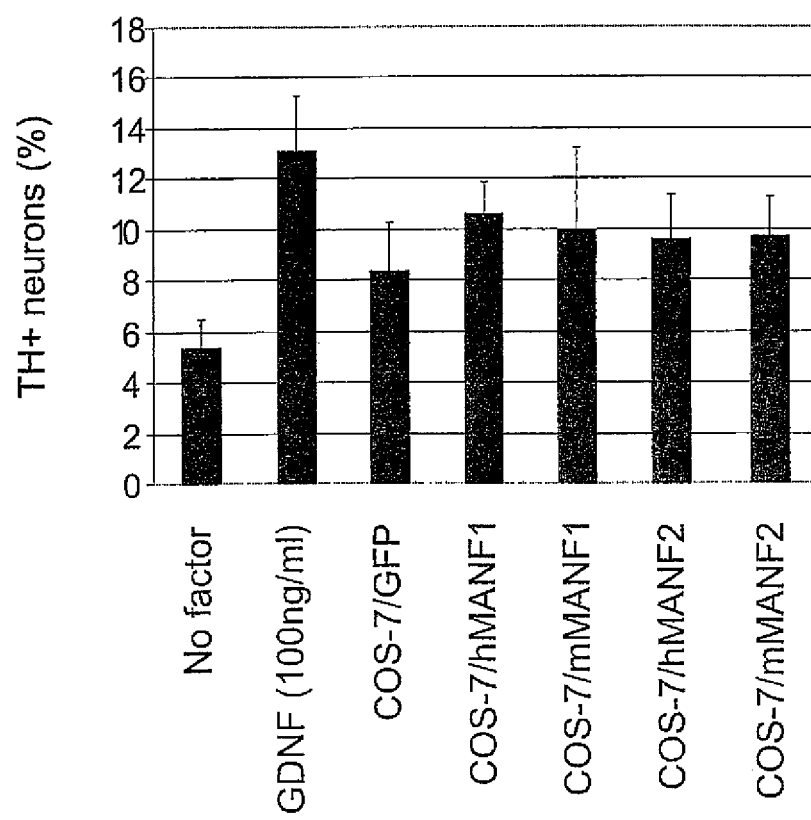
Figure 11.

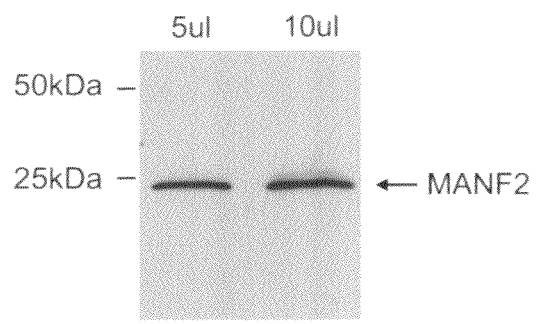
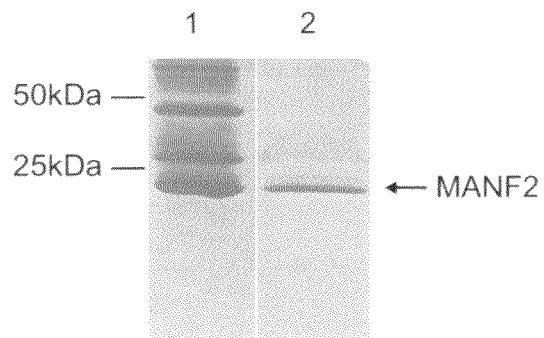
Figure 13.

A
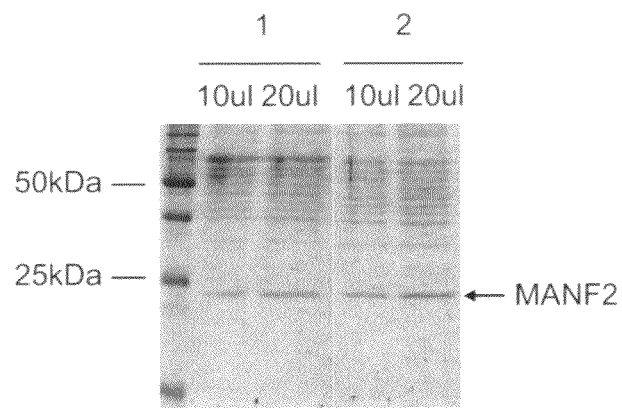
B
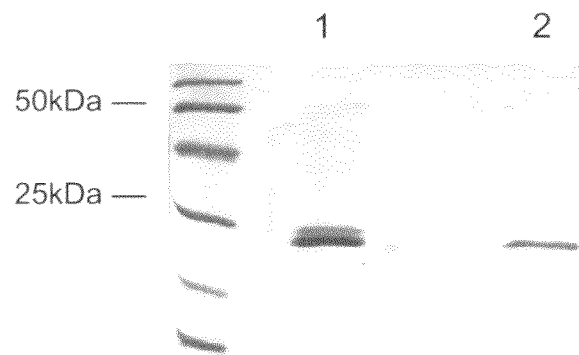
Figure 14.

Figure 15

>*Homo sapiens* MANF2 protein

MWCASPVAVVAFCAGLLVSHPVLTQG*QEAGGRPGADCEVCKEFLNRFYKSLID
RGVNFSLDTIEKELISFCLDTKGKENRLCYYLGATKDAATKILSEVTRPMSVHMPA
MKICEKLKKLDSQICELKYEKTLDLASVDLRKMRVAELKQILHSWGEECRACAEK
TDYVNLIQELAPKYAATHPKTEL

MANF2 FOR TREATMENT OF PARKINSON'S DISEASE

This application is a Divisional of U.S. application Ser. No. 11/330,359, filed on Jan. 12, 2006, now abandoned, which is a Continuation-In-Part of U.S. application Ser. No. 10/648,361, filed on Aug. 27, 2003, now U.S. Pat. No. 7,452,969, which claims the benefit of priority under 35 USC 119 (e) of U.S. Provisional Application No. 60/1406,927, flied on Aug. 30, 2002, and Ser. No. 11/330,359 is a continuation of PCT International Application No. PCT/FI2005/050461, filed on Dec. 14, 2005. The entire contents of all of these applications are hereby incorporated b reference.

FIELD OF THE INVENTION

The present invention generally relates to the field of genetic engineering and more particularly to growth factors for neural cells, especially for dopaminergic neurons at the CNS (central nervous system) and growth factor genes.

BACKGROUND OF THE INVENTION

Studying the mechanisms of regulation of the neuronal fate is of importance to understand the determination, differentiation, and maintenance of neurons. Second, identification of extracellular and intracellular regulators that are important in determining the neuronal phenotype, has attracted considerable interest because of the possible therapeutic importance in treatment of several neurodegenerative diseases. The role of extracellular signals in determining the diversity of vertebrate nervous system has been studied extensively. The most well characterised of the secreted factors involved in the control of developing and adult nervous system are the nerve growth factor (NGF) and the glial-cell derived neurotrophic factor (GDNF) families of neurotrophic factors (reviewed in Bibel and Barde, 2000, Genes Dev 14:2919-2937; Airaksinen et al 1999, Mol Cell Neurosci 13:313-325; Airaksinen and Saarma 2002, Nat Rev Neurosci 2002 3:383-394). These neurotrophic factors promote survival, differentiation and maintenance of specific neuronal populations in vertebrates. Later it has been shown that they have other important functions, including regulation of activity-dependent synaptic plasticity, stimulation of neurite outgrowth, and protection and repair of neurons during tissue injury.

SUMMARY OF THE INVENTION

The present invention discloses a novel neurotrophic factor protein, MANF2 and a genetic sequence encoding the same. The molecule will be useful in the development of a range of therapeutics and diagnostics useful in the treatment, prophylaxis and/or diagnosis of MANF2 dependent conditions. The molecule of the present invention is also a useful effector of primary and central neurons.

Recently a new human neurotrophic factor, the mesencephalic astrocyte-derived neurotrophic factor (MANF1 hereby named MANF1) was identified and shown to protect the survival of embryonic mesencephalic dopaminergic neurons in culture (patent application WO0119851). MANF1 is a 20 kD secreted protein with no significant homology to other known protein families. The in vitro properties of MANF1 suggest that it could be used for the treatment of Parkinson's disease and possibly, for the treatment of other neurodegenerative diseases. The wide expression pattern of MANF1 however (Shridhar et al, 1996, Oncogene 12:1931-1939) also suggest that it may have other yet undiscovered functions outside nervous system, and effects on many different cell types.

MANF1 is, therefore, an important molecule making it a potentially valuable target for research into therapeutics, prophylactics and diagnostic agents based on MANF1 or its activities. There is also a need to identify homologues or otherwise related molecules for use as an alternative to MANF1 or in conjunction with MANF1.

In work leading up to the present invention, the inventors discovered a novel molecule named as MANF2, which is a new growth factor related to MANF1.

Accordingly, one preferred aspect of the present invention comprises an isolated protein molecule comprising the amino acid sequence of SEQ ID NO:2 of FIG. 7 or mutations, variants or fragments thereof.

In a particularly preferred embodiment, the MANF2 molecule of the present invention comprises a sequence of amino acids as set forth in SEQ ID NO:2 of FIG. 7 or is a part, fragment, derivative or analogue thereof. Particularly preferred similarities include about 19-20%, and 29-30%. Preferably, the percentage similarity is at least about 30%, more preferably at least about 40%, still more preferably at least about 50%, still even more preferably at least about 60-70%, yet even more preferably at least about 80-95% to all or part of the amino acid sequence set forth in SEQ ID NO:2 of FIG. 7.

In still another preferred aspect of the invention provides the molecule in recombinant form.

Still a further aspect of the present invention contemplates a peptide fragment corresponding to a portion of the amino acid sequence set forth in SEQ ID NO:2 of FIG. 7 or a chemical equivalent thereof. The isolated or recombinant molecule of the present invention may be naturally glycosylated or may comprise an altered glycosylation pattern depending on the cells from which it is isolated or synthesised. For example, if produced by recombinant means in prokaryotic organisms, the molecule would be non-glycosylated. The molecule may be a full length, naturally occurring form or may be a truncated or otherwise derivatised form.

Also disclosed are optionally formulated MANF2 polypeptide pharmaceutical compositions. Polypeptide compositions of the present invention may further comprise an acceptable carrier, such as a hydrophilic, e.g., pharmaceutically acceptable, carrier. Such compositions are useful in treating MANF2 dependent conditions.

One preferred aspect is antibodies that specifically bind to MANF2. Preferred antibodies are monoclonal antibodies that are non-immunogenic in a human. Preferred antibodies bind the MANF2 with an affinity of at least about $10^{-6}$ M, more preferably $10^{-7}$ M.

The present invention also contemplates antibodies to the MANF2 molecule or nucleic acid probes to a gene encoding the MANF2 molecule which are useful as diagnostic agents.

In a further aspect is provided a method for detecting MANF2 in vitro or in vivo which includes the steps of contacting an MANF2 antibody with a sample suspected of containing the MANF2, and detecting if binding has occurred.

The invention also includes a kit and reagents for diagnosing a MANF2-dependent disorder in a mammal. The kit comprises a reagent which detects the presence or absence of a mutation in the nucleic acid sequence encoding MANF2, elevated or diminished levels of MANF2 polypeptide and/or MANF2 antibody. The presence of the mutation or abnormal levels of MANF2 is an indication that the mammal is afflicted with the MANF2-dependant disorder. The kit further comprises an applicator and an instructional material for the use thereof.

In addition to the above, the invention provides isolated nucleic acid molecules, expression vectors and host cells encoding MANF2 which can be used in the recombinant production of MANF2 as described herein. The isolated nucleic acid molecules and vectors are also useful to prepare transgenic animals and for gene therapy applications to treat patients with MANF2 defects.

The MANF2 molecule of the present invention will be useful in the development of a range of therapeutic and/or diagnostic applications alone or in combination with other molecules such as MANF1. The present invention extends, therefore, to pharmaceutical compositions comprising the MANF2 molecule or parts, fragments, derivatives, homologues or analogues thereof together with one or more pharmaceutically acceptable carriers and/or diluents. Furthermore, the present invention extends to vectors comprising the nucleic acid sequence set forth in SEQ ID NO:1 of FIG. 7 or having at least about 15%, more preferably about 40%, even more preferably around 60-79% or even still more preferably around 80-95% similarity thereto and host cells comprising the same.

In one embodiment the isolated MANF2 polynucleotides have at least 80% sequence identity to the sequence set forth in SEQ ID NO:1 or SEQ ID NO:3 of FIG. 7, or a complement thereof.

The present invention also contemplates genomic or partial genome clones encoding a proteinaceous molecule having at least about 15% amino acid similarity but at least about 5% dissimilarity to SEQ ID NO:2.

The instant invention also contemplates the homologous molecule and encoding sequence from other mammals such as livestock animals (e.g. sheep, pigs, horses and cows), companion animals (e.g. dogs and cats) and laboratory test animals (e.g. mice, rats, rabbits and guinea pigs) as well as non-mammals such as birds (e.g. poultry birds), fish and reptiles. In a most preferred embodiment, the MANF2 molecule is of human origin. The present invention extends, therefore, to the human genomic sequence or part thereof encoding the MANF2 molecule.

Yet another aspect of the present invention is directed to a nucleic acid molecule encoding the MANF2 molecule herein described. More particularly, the present invention provides a nucleic acid molecule comprising a sequence of nucleotides substantially as set forth in SEQ ID NO:1 of FIG. 7 or having at least 15% similarity to all or part thereof or being capable of hybridising under low stringency conditions to a reverse complement of the nucleotide sequence as set forth in SEQ ID NO:1 of FIG. 7 provided that the nucleic acid sequence having at least 15% similarity but at least 5% dissimilarity to the nucleotide sequence as set forth in SEQ ID NO:1 of FIG. 7.

For the purposes of defining the level of stringency, reference can conveniently be made to Sambrook et al, Molecular Cloning: A Laboratory Manual (New York: Cold Spring Harbor Laboratory Press, 1989) at pages 9.47-9.51 which is herein incorporated by reference where the washing steps disclosed are considered high stringency. A low stringency is defined herein as being in 4-6×SSC/0.1-0.5% w/v SDS at 37-45 degree of C for 2-3 hours. Depending on the source and concentration of nucleic acid involved in the hybridisation, alternative conditions of stringency may be employed such as medium stringent conditions which are considered herein to be 1-4×SSC/0.25-0.5% w/v SDS at 45 degree of Celsius for 2-3 hours or high stringent conditions considered herein to be 0.1-1×SSC/0.1% w/v SDS at 60 degree of Celsius for 1-3 hours.

In another embodiment the present invention is a transgenic non-human animal having a disrupted MANF2 gene or a transgenic non-human animal expressing an exogenous polynucleotide having at least 80% sequence identity to the sequence SEQ ID NO:2 or SEQ ID NO:4 of FIG. 7, or a complement of said polynucleotide.

In another embodiment the present invention can be used for a method of treating various pathologies, including neurological diseases such as Parkinson's disease or Alzheimers disease.

In another embodiment the present invention is a method of screening a tissue sample for MANF2 nucleotide sequence.

Although methods and materials similar or equivalent to those described herein can be used in the practice or testing of the present invention, suitable methods and materials are described below. The materials, methods, and examples are illustrative only and not intended to be limiting.

BRIEF DESCRIPTION OF THE DRAWINGS

FIG. 1. Alignment of *Homo sapiens* MANF1 and MANF2 amino acid sequences. (SEQ ID NOS:13 and 2, respectively) The alignment was generated with ClustalX program. Identical amino acid residues are marked with asterisk; based on the physicochemical characteristics of the residues high similarity is marked with a double colon and similarity with a dot. Signal sequences are underlined. Secondary structure alpha helix motifs are conserved between MANF1 and MANF2 and are marked above the sequences. Also the eight conserved cysteines are marked (boxed).

FIG. 2. Alignment of *Homo sapiens* and *Mus musculus* MANF2 amino acid sequences. (SEQ ID NOS: 2 and 4, respectively) For explanations of the symbols, see FIG. 1.

FIG. 3. Alignment of MANF amino acid sequences from selected organisms. The sequences were acquired by running Blast searches at the National Center for Biotechnology Information's www-server www.ncbi.nlm.nih.gov). In some cases the sequence was assembled from the genomic sequence and in some cases by assembling overlapping expressed sequence tags.

*Mus musculus*—MANF1 (SEQ ID NO: 14)
*Rattus norvegivus* (SEQ ED NO: 15)
*Homo sapiens*—MANF1 (SEQ ID NO:13 (residues 27-179))
*Bos Taurus* (SEQ ID NO: 16)
*Gallus gallus* (SEQ ID NO: 17)
*Xenopus laevis* (SEQ ID NO: 18)
*Fugu rubribes* (SEQ ID NO: 19)
*Danio rerio* (SEQ ID NO: 20)
*Homo sapiens*—MANF2 (SEQ ID NO: 2 (residues 37-187))
*Mus musculus*—MANF2 (SEQ ID NO: 4 (residues 37-187))
*Drosophila melanogaster* (SEQ ID NO: 21)
*Canorhabditis elegans* (SEQ ID NO: 22)

FIG. 4. Dendrogram of MANF family proteins from selected organisms.

FIG. 5. Analysis of human MANF2 expression in different tissues analysed by RT-PCR. Primers amplifying full-length human MANF2 genes (h-MANF2-atg and h-MANF2-stop-del) were used in PCR with Dynazyme DNA polymerase (Finnzymes) and Dynazyme 10× buffer. Total volume of PCR reaction was 25 ul. Annealing temperature of 55 degrees of Celsius and extension time of 30 seconds were used with totally 35 cycles in PCR. In FIG. 5C Primers h-MANF2-atg and h-MANF2-int-as were used.

FIG. 5A: Lanes: 1 adrenal gland, 2 bone marrow, 3 foetal brain, 4 adult brain, 5 cerebellum, 6 colon, 7 heart, 8 kidney, 9 foetal liver, 10 adult liver, 11 lung, 12 mammary gland, 13 muscle, 14 pancreas.

FIG. 5B: Lanes: 1 placenta, 2 prostate, 3 salivary gland, 4 small intestine, 5 spinal cord, 6 spleen, 7 stomach, 8 testis, 9 thymys, 10 thyroid, 11 trachea, 12 uterus, 13 water.

FIG. 5C: Lanes: 1 hippocampus, 2 thalamus, 3 amygdala, 4 corpus callosum, 5 cerebellum, 6 caudate nucleus, 7 cerebral cortex, 8 substantia nigra, 9 fetal brain, 10 brain, 11 water.

Figure 6:
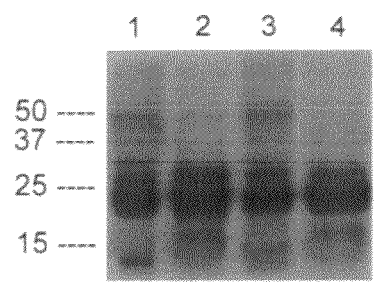

FIG. 6. Analysis of recombinant human and mouse MANF2 protein as expressed in COS7 cells. Expression constructs containing full-length human and mouse MANF2 genes with carboxy-terminal hexahistidine and V5 tags were generated by cloning full-length coding cDNAs without stop-codons into pcDNA3.1 expression vector (Invitrogen). Cos7 cells grown in DMEM with 10% FCS and antibiotics were plated on 35 mm plates and transfected with 4 ug of plasmid when grown up to approximately 70% confluence. Media was replaced with serum free media 24 hrs after transfection. The cells and supernatants were collected 72 hrs postransfection. Protein from 15% denaturating SDS-PAGE gel was blotted into nylon membrane, blocked with 5% BSA in TBS-Tween (0.1%) and detected with mouse anti-V5 antibody (1:5000 dilution) and HRP-conjugated goat anti-mouse immunoglobulin secondary antibody (1:2000 dilution) by using ECL method. Lane 1 Cells transfected with expression vector encoding human MANF2 gene, cell lysate; Lane 2 Cells transfected with expression vector encoding human MANF2 gene transfected cells, supernatant; Lane 3 Cells transfected with expression vector encoding mouse MANF2 gene, cell lysate; Lane 4 Cells transfected with expression vector encoding mouse MANF2 gene, supernatant.

FIG. 7. Amino acid and nucleic acid sequences of MANF2 in *Homo sapiens* and *Mus Musculus*. (SEQ ID NOS: 1-4)

Figure 8:
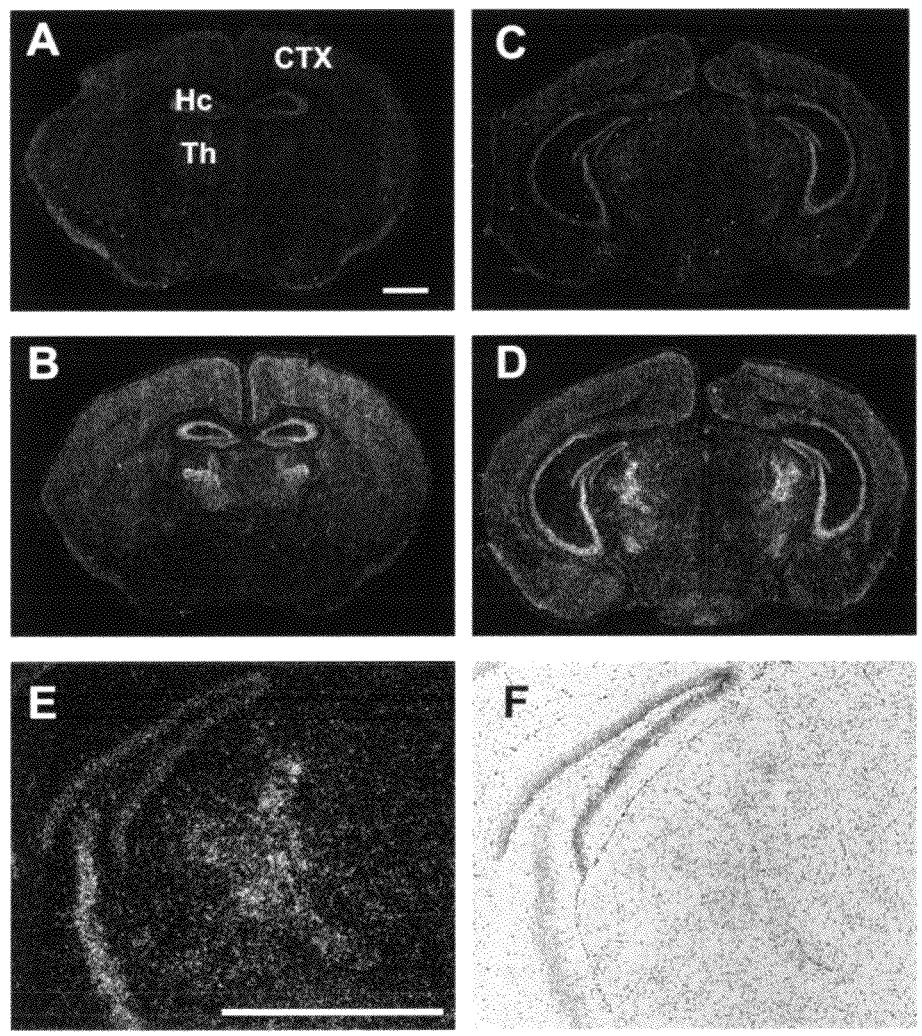

FIG. 8. Expression of MANF2 mRNA in P10 mouse brain by in situ hybridization. Coronal sections were hybridized with sense (A,C) and antisense (B,D,E,F) cRNA probes and photographed under dark-field and bright-field illumination. MANF2 mRNA was detected mainly in thalamus and hippocampus when compared with sense controls. F, silver grains localized in thalamus. In postnatal and adult brain, MANF2 mRNA expression pattern is more restricted as compared with expression of MANF1 mRNA, and expression level lower than that of MANF1. During mouse embryonic development, MANF2 mRNA was not expressed at detectable levels as measured by in situ hybridization. CTX, cerebral cortex; Th, thalamus; Hc, hippocampus. Scale bar 1 mm.

Figure 9:
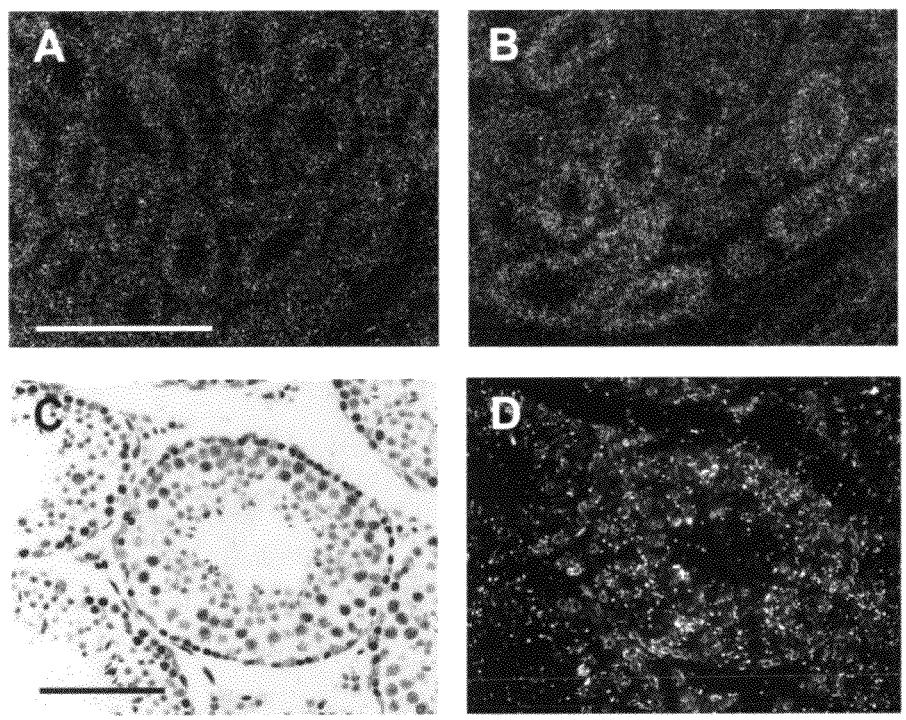

FIG. 9. MANF2 mRNA expression in seminiferous tubuli in adult mouse testis as detected by in situ hybridization. Sections were hybridized with sense (A) and antisense (B, C, D) cRNA probes and photographed under dark-field and bright-field illumination. Scale bar 500 μm in A and B, 100 μm in C and D.

Figure 10:
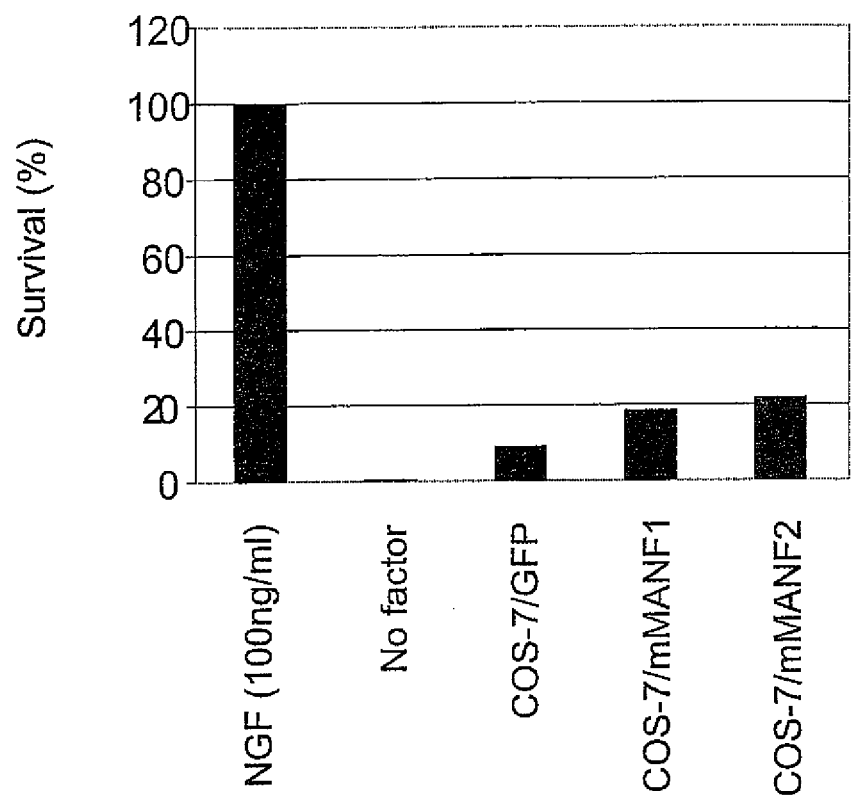

FIG. 10. Recombinant MANF2 protein from COS-7 cells promotes survival of E16 mouse dorsal root ganglion (DRG) neurons in vitro. Supernatants from COS-7 cells transiently transfected with mouse MANF2 in pcDNA3.1 or MANF1 in pcDNA3.1, or with GFP (pGreenLantern, Gibco) were collected and concentrated. MANF2 and MANF1 proteins were applied on neuronal cultures at concentration of 100 ng/ml. Cells were cultured for 6 days, and live neurons were counted. Lanes: 1, NGF (100 ng/ml); 2, no factor added; 3, COS-7/GFP; 4, COS-7/mouse MANF1; 5, COS-7/mouse MANF2.

FIG. 11. Recombinant MANF2 protein produced in COS-7 cells promotes survival of E14 rat dopamine neurons in vitro. Supernatants from COS-7 cells transiently transfected with mouse or human MANF2 in pcDNA3.1, mouse or human MANF1 in pcDNA3.1 or with GFP (pGreenLantern, Gibco) were collected and concentrated. To test survival promoting activity, MANF proteins were applied to dopamine cell cultures at concentration of 100 ng/ml. Supernatant from GFP transfected cells and GDNF (100 ng/ml) was used as negative and positive controls, respectively. Cells were cultured for 6 days, fixed and stained with anti-TH-antibody. Both human and mouse MANF2 promoted survival of dopaminergic neurons as efficiently as human and mouse MANF1. Lanes in panels A and B: 1, no factor added; 2, GDNF; 3, COS-7/GFP; 4, COS-7/human MANF1; 5, COS-7/mouse MANF1; 6, COS-7/human MANF2; 7, COS-7/mouse MANF2.

Figure 12:
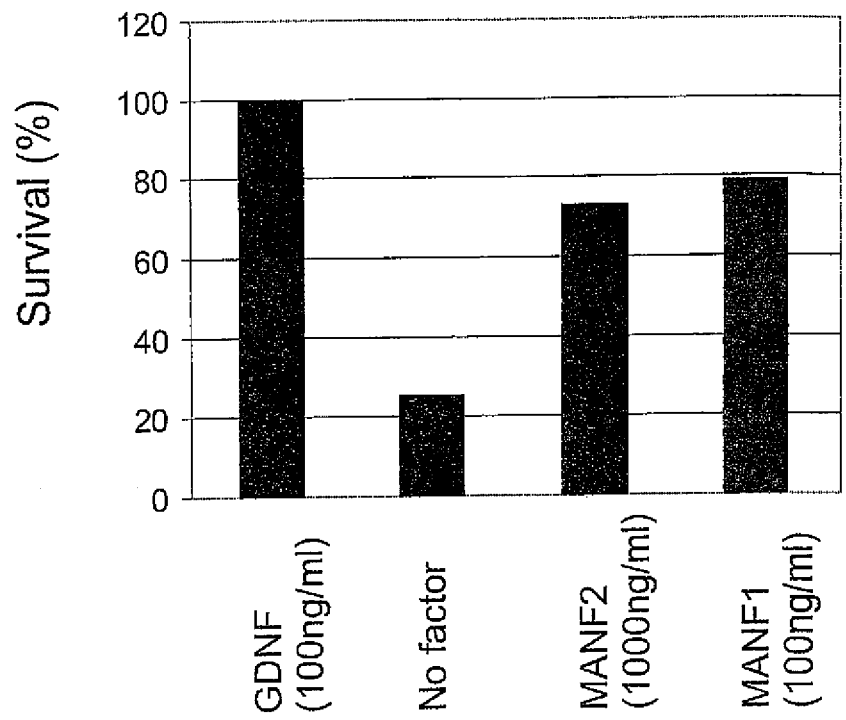

FIG. 12. Recombinant MANF2 protein produced in Sf9 cells promotes survival of E13 mouse dopamine neurons in vitro. Stable Sf9 cell line secreting human MANF2 was established, and MANF2 protein was purified from conditioned medium Dopamine neurons were cultured with or without factors for 6 days, fixed and stained with anti-TH-antibody. Experiment was repeated with equal results. Lanes: 1, GDNF (10 ng/ml); 2, no factor added; 3, MANF2 (1000 ng/ml); 4, MANF1 (100 ng/ml).

FIG. 13. Purification of MANF2 protein from Sf9-hMANF2 stable cell line.

A. Western blot with anti-V5-antibody showing protein secretion.

B. Lane 1, Sample after purification step 1 and lane 2, after step 2.

FIG. 14. Purification of MANF2 protein from COS-7 cell supernatant.

A. His-tagged mouse (lane 1) and human (lane 2) MANF2 after purification step 1. COS-7 cells were transiently transfected with mouse or human MANF2 in pcDNA3.1, culture medium was collected and His-tagged proteins were precipitated with Ni-sepharose and eluted with imidazole. Part of elute (10 or 20 ul) was loaded on a 15% SDS-PAGE gel, and proteins were stained with Coomassie stain.

B. Recombinant MANF1 (lane 1) and MANF2 (lane 2) proteins purified by reversed phase chromatography and blotted on a PVDF membrane.

FIG. 15. Human MANF2 protein (SEQ ID NO: 2) secretory signal cleavage site. Recombinant MANF2 protein containing original signal sequence was produced in COS-7 cells. Purified protein was subjected to tryptic digest, and peptide fragments were analyzed by Q-TOF mass spectrometry. Analysis verified the signal sequence cleavage site between amino acids at position 26 and 27.

Figure 16:
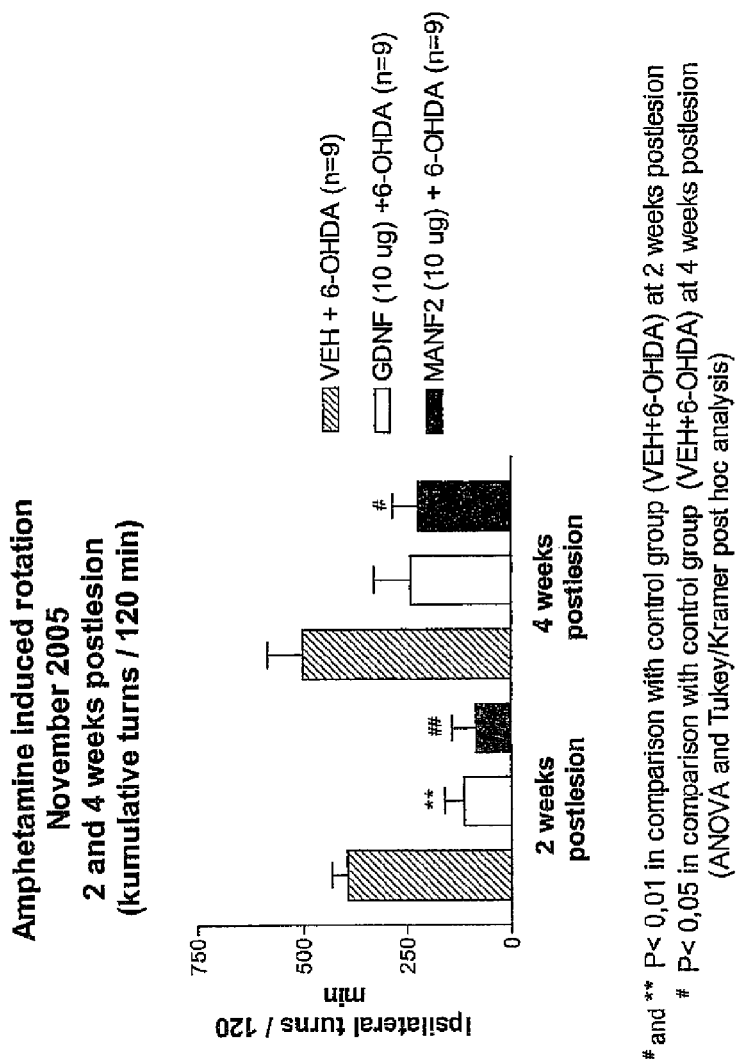

FIG. 16. MANF2: Behavioral tests. A single injection of MANF2 six hours before 6-OHDA delivery into the dorsal striatum of adult rats significantly reduced the amphetamine-induced ipsilateral turning behavior at 2 and 4 weeks post-lesion.

Figure 17:
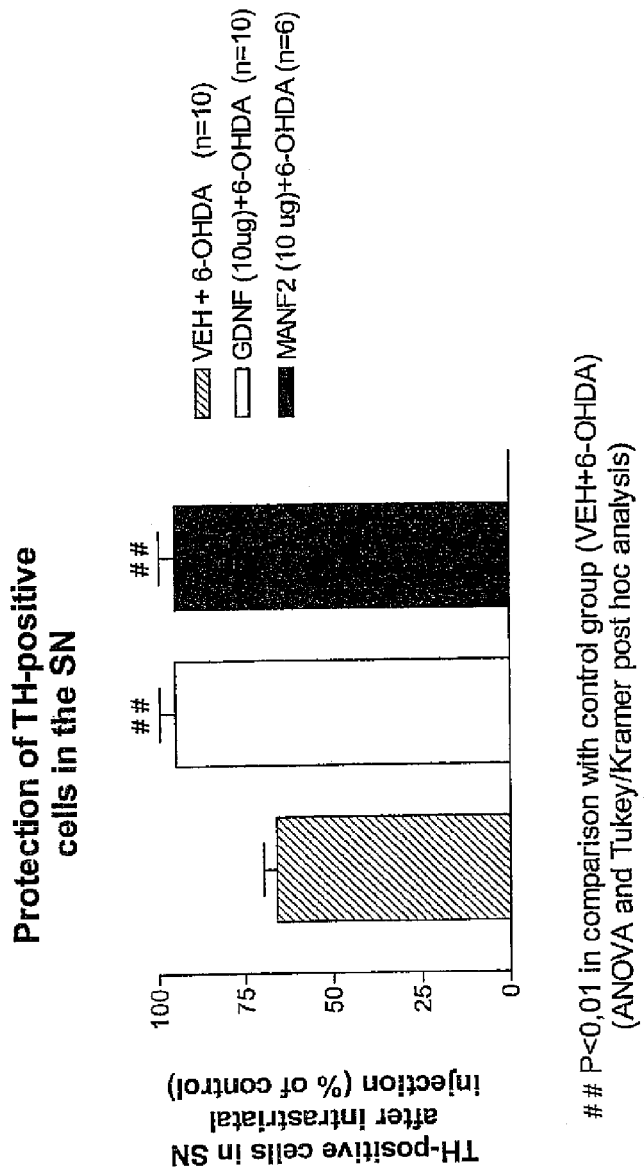

FIG. 17. Morphological analysis. A single injection of MANF2 six hours before 6-OHDA delivery into the dorsal striatum of adult rats almost completely rescued tyrosine hydroxylase positive cells in the substantia nigra.

DETAILED DESCRIPTION OF THE INVENTION

By performing Blast-searches at the National Center for Biotechnology Information (NCBI) of the National Library of Medicine's (NLM) www-server (See Altschul et al. "Gapped BLAST(R) and PSI-BLAST: a new generation of protein database search programs", Nucleic Acids Res. 25

(1997): 3389-3402), we identified several human and mouse EST (expressed sequence tag) cDNAs that share high level of sequence similarity to MANF1. However, none of the human ESTs contained a fall open reading frame of an obvious MANF1 homolog as many of them contained insertions, deletions and 5' ends of different length that shared no homology with MANF1.

We assembled several partial human EST cDNA clones that were homologous to MANF1 into a contig and we designed primers (see Example 1) for the cloning of a full length cDNA of a possible MANF1 homolog from human and mouse. Surprisingly, we were able to clone full-length mouse and human cDNAs by RT-PCR from brain and named them mouse and human MANF2 (see FIG. 7 for nucleic acid and amino acid sequences of human and mouse MANF2).

Both human and mouse MANF2 cDNAs encode 187 amino acid proteins (FIGS. 1 and 2). The overall amino acid sequences of human MANF1 and human MANF2, and mouse MANF1 and mouse MANF2 share about 65% identity respectively (see Table A). Both MANF1 and MANF2 protein have a unique pattern of eight conserved cysteines. Bioinformatic analyses showed that human MANF2 is encoded by a relatively small gene coded by four exons, located in chromosome 10. Secondary structure of human and mouse MANF2 proteins, similarly to MANF1 protein, is dominated by alpha-helices and random coils. Furthermore, bioinformatic analyses of genome and EST sequences from various organisms suggest that mammals have two MANF genes, the fish, amphibians and birds at least one MANF gene and the nematode *Caenorhabditis elegans* and the fruitfly *Drosophila melanogaster* one MANF gene (FIGS. 3 and 4).

We also analyzed the expression of MANF2 mRNA by RT-PCR. The results showed that MANF2 mRNA is widely but in relatively low levels expressed in all 26 different human tissues and in eight different human brain regions that were analyzed. The expression levels varied somewhat between different tissues. In the brain, MANF2 mRNA levels are lower in fetal brain as compared to the adult brain (FIG. 5). Similar results were obtained for mouse MANF2 expression.

To study if MANF2 protein is secreted we generated expression constructs encoding V5-His-tagged human MANF2 fusion proteins and analyzed their expression and secretion in Cos-7 cells. The results showed that MANF2 is a secreted ~20 kDa protein, with potential glycosylation and/or posttranslational processing (cleavage) involved (FIG. 6).

TABLE A

MANF1 vs MANF2

| | Hs-MANF1 | Hs-MANF2 | Mm-MANF1 | Mm-MANF2 |
|---|---|---|---|---|
| Amino acid identity (%)* | | | | |
| Hs-MANF1 | 100 | — | — | — |
| Hs-MANF2 | 65 | 100 | — | — |
| Mm-MANF1 | 98 | 63 | 100 | — |
| Mm-MANF2 | 65 | 80 | 65 | 100 |
| Amino acid similarity (%)* | | | | |
| Hs-MANF1 | 100 | — | — | — |
| Hs-MANF2 | 79 | 100 | — | — |
| Mm-MANF1 | 98 | 78 | 100 | — |
| Mm-MANT2 | 78 | 88 | 78 | 100 |

*Signal sequences omitted

Unless defined otherwise, all technical and scientific terms have the same meaning as is commonly understood by one of skill in the art to which this invention belongs. The definitions below are presented for clarity.

"Isolated" when referred to a molecule, refers to a molecule that has been identified and separated and/or recovered from a component of its natural environment and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide sequences of the present invention.

As used herein, a "polynucleotide" refers to a molecule having a nucleic acid sequence encoding SEQ ID NO:1 of FIG. 7 or a fragment or variant thereof, a nucleic acid sequence contained in SEQ ID NO:3 of FIG. 7 or the complement thereof. For example, the polynucleotide can contain the nucleotide sequence of the full-length cDNA sequence, including the 5' and 3' untranslated sequences, the coding region, as well as fragments, epitopes, domains, and variants of the nucleic acid sequence. Moreover, as used herein, a "polypeptide" refers to a molecule having an amino acid sequence encoded by a polynucleotide of the invention as broadly defined. As used herein, the term "fragment" as applied to a nucleic acid, may ordinarily be at least about 10 nucleotides in length, typically, at least about 20 nucleotides, more typically, from about 20 to about 50 nucleotides, preferably at least about 50 to about 100 nucleotides, even more preferably at least about 100 nucleotides to about 300 nucleotides, yet even more preferably at least about 300 to about 400, and most preferably, the nucleic acid fragment will be greater than about 500 nucleotides in length.

As used herein, the term "fragment" as applied to a polypeptide, may ordinarily be at least about seven contiguous amino acids, typically, at least about fifteen contiguous amino acids, more typically, at least about thirty contiguous amino acids, typically at least about forty contiguous amino acids, preferably at least about fifty amino acids, even more preferably at least about sixty amino acids and most preferably, the peptide fragment will be greater than about seventy contiguous amino acids in length.

"Nucleic acid molecule", includes DNA molecules (e.g. cDNA or genomic DNA), RNA molecules (e.g., mRNA), analogs of the DNA or RNA generated using nucleotide analogs, and derivatives, fragments and homologs. The nucleic acid molecule may be single-stranded or double-stranded, but preferably comprises double-stranded DNA.

"Isolated nucleic acid molecule" is separated from other nucleic acid molecules which are present in the natural source of the nucleic acid. Preferably, an isolated nucleic acid is free of sequences that naturally flank the nucleic acid (i.e. sequences located at the 5'- and 3'-termini of the nucleic acid) in the genomic DNA of the organism from which the nucleic acid is derived. For example, in various embodiments, isolated MANF2 DNA molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an isolated nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a MANF2 nucleic acid molecule, or a complement of this aforementioned nucleotide sequence, can be isolated using standard molecular biology techniques and the provided sequence information. Using all or a portion of a MANF2 nucleic acid sequence of interest as a hybridization probe, MANF2 molecules can be isolated using standard hybridization and cloning techniques (Ausubel et al, In Current protocols in Molecular Biology, John Wiley and Sons, publishers, 1989); Sambrook et al, supra).

"Analogs" are nucleic acid sequences or amino acid sequences that have a structure similar to, but not identical to, the native compound but differ from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions (Ausubel et al., supra).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Control sequences" are DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

"Operably-linked nucleic acid" is operably-linked when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Oligonucleotide" comprises a series of linked nucleotide residues, which oligonucleotide has a sufficient number of nucleotide bases to be used in a PCR reaction or other application. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

"Stringency". Homologs (i.e., nucleic acids encoding MANF2 molecules derived from species other than human) or other related sequences (e.g., paralogs) can be obtained by low, moderate or high stringency hybridization with all or a portion of the particular human sequence as a probe using methods well known in the art for nucleic acid hybridization and cloning.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favour specific hybridizations (high stringency), which can be used to identify, for example, full-length clones from a library. Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach is to vary the temperature: higher relative temperatures result in more stringent reaction conditions. (Ausubel et al., supra) provide an excellent explanation of stringency of hybridization reactions.

To hybridize under "stringent conditions" describes hybridization protocols in which nucleotide sequences at least 60% homologous to each other remain hybridized. Generally, stringent conditions are selected to be about 5 degrees of Celsius lower than the thermal melting point (Tm) for the specific sequence at a defined ionic strength WO 01/70174 PCT/US01/0904330. Low stringency "low stringent conditions" use washing solutions and hybridization conditions that are less stringent than those for moderate stringency (Sambrook, supra), such that a polynucleotide will hybridize to the entire, fragments, derivatives or analogs of a target MANF2 target sequence. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40 degrees of Celsius, followed by one or more washes in 2×SSC, 25 mM Tris-HCl (pH 7.4), 5 mM EDTA, and 0.1% SDS at 50 degrees of Celsius. Other conditions of low stringency, such as those for cross-species hybridizations are described in (Ausubel et al., supra; Kriegler M P (1990) Gene transfer and expression; a laboratory manual; Shilo and Weinberg, Proc. Natl. Acad. Sci. USA 78:6789-6792 (1981)).

PCR amplification techniques can be used to amplify MANF2 using cDNA, mRNA or alternatively, genomic DNA, as a template and appropriate oligonucleotide primers. Such nucleic acids can be cloned into an appropriate vector and characterized by DNA sequence analysis. Furthermore, oligonucleotides corresponding to MANF2 sequences can be prepared by standard synthetic techniques, e.g., an automated DNA synthesizer.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded.

Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the nucleic acid encoding the desired protein, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5.3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

"Probes" are nucleic acid sequences of variable length, preferably between at least about 10 nucleotides (nt), 100 nt, or many (e.g., 6000 nt) depending on the specific use. Probes are used to detect identical, similar, or complementary nucleic acid sequences. Longer length probes can be obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies. Probes will also hybridize to nucleic acid molecules in biological samples, thereby enabling immediate applications in chromosome mapping, linkage analysis, tissue identification and/or typing, and a variety of forensic and diagnostic methods of the invention.

Probes are substantially purified oligonucleotides that will hybridize under stringent conditions to at least optimally 12, 25, 50, 100, 150, 200, 250, 300, 350 or 400 consecutive sense strand nucleotide sequence; or an anti-sense strand nucleotide sequence; or of a naturally occurring mutant of the MANF2 DNA sequence of interest.

The full- or partial length native sequence MANF2 DNA may be used to "pull out" similar (homologous) sequences (Ausubel et al., supra; Sambrook, supra), such as: (1) full-length or fragments of MANF2 cDNA from a cDNA library from any species (e.g. human, murine, feline, canine, bacterial, viral, retroviral, yeast), (2) from cells or tissues, (3) variants within a species, and (4) homologues and variants from other species. To find related sequences that may encode related genes, the probe may be designed to encode unique sequences or degenerate sequences. Sequences may also be genomic sequences including promoters, enhancer elements and introns of native MANF2 sequence.

To detect hybridizations, probes are labeled using, for example, radionuclides such as 32P or 35S, or enzymatic labels such as alkaline phosphatase coupled to the probe via avidin-biotin systems. Labeled probes are used to detect nucleic acids having a complementary sequence to that of MANF2 in libraries of cDNA, genomic DNA or mRNA of a desired species. Such probes can be used as a part of a diagnostic test kit for identifying cells or tissues which mis-express a MANF2, such as by measuring a level of a MANF2 in a sample of cells from a subject e.g., detecting MANF2 mRNA levels or determining whether a genomic MANF2 has been mutated or deleted.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Homologs" are nucleic acid sequences or amino acid sequences of a particular gene that are derived from different species.

A "homologous nucleic acid sequence" or "homologous amino acid sequence," or variations thereof, refer to sequences characterized by a homology at the nucleotide level or amino acid level. Homologous nucleotide sequences encode those sequences coding for isoforms of MANF2. Isoforms can be expressed in different tissues of the same organism as a result of, for example, alternative splicing of RNA. Alternatively, different genes can encode isoforms. In the invention, homologous nucleotide sequences include nucleotide sequences encoding for a MANF2 of species other than humans, including, but not limited to vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding a human MANF2. Homologous nucleic acid sequences include those nucleic acid sequences that encode conservative amino acid substitutions in a MANF2 sequence of interest, as well as a polypeptide possessing MANF2 biological activity.

"Percent (%) nucleic acid sequence identity" with respect to a MANF2 is defined as the percentage of nucleotides in a candidate sequence that are identical with the nucleotides in that particular MANF2, after aligning the sequences and introducing gaps, if necessary, to achieve the maximum percent sequence identity.

Alignment for purposes of determining % nucleic acid sequence identity can be achieved in various ways that are within the skill in the art, for instance, using publicly available computer software such as BLAST, BLAST-2, ALIGN, Megalign (DNASTAR) or ClustalX software. Those skilled in the art can determine appropriate parameters for measuring alignment, including any algorithms needed to achieve maximal alignment over the full length of the sequences being compared.

BLAST protein searches can be performed with the XBLAST program (designated "blastn" at the NCBI web site) or the NCBI "blastp" program, using the following parameters: expectation value 10.0, BLOSUM 62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25: 3389-3402). Alternatively, PSI-Blast or PHI-Blast can be used to perform an iterated search which detects distant relationships between molecules and relationships between molecules which share a common pattern. When utilizing BLAST, Gapped BLAST, PSI-Blast, and PHI-Blast programs, the default parameters of the respective programs (e.g., XBLAST and NBLAST) can be used. www.ncbi.nlm.nih.gov.

The "open reading frame" (ORF) of a MANF2 gene encodes MANF2. An ORF is a nucleotide sequence that has commonly a start codon (ATG) and terminates commonly with one of the three "stop" codons (TAA, TAG, or TGA). In this invention, however, an ORF—may be any part of a coding sequence that may or may not comprise a start codon and a stop codon. To achieve a unique sequence, preferable MANF2—ORFs encode at least 50 amino acids.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic nonnaturally occurring analogs thereof linked via peptide bonds, related naturally occurring structural variants, and synthetic non-naturally occurring analogs thereof. Synthetic polypeptides can be synthesized, for example, using an automated polypeptide synthesizer.

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope can be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an antimyc-monoclonal antibody affinity matrix, a glutathione-S-transferase tag epitope, and a maltose binding protein (MBP) tag epitope, which can induce binding between a protein comprising such an epitope and a glutathione- or maltose Sepharose column, respectively. Production of proteins comprising such tag epitopes is well known in the art and is described in standard treatises such as Sambrook et al., supra, and Ausubel et al., supra. Likewise, antibodies to the tag epitope allow detection and localization of the fusion protein in, for example, Western blots, ELISA assays, and immunostaining of cells.

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab') and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567 (Cabilly et al.)). The "monoclonal antibodies" may also be isolated from phage antibody libraries using the techniques described in Clackson et al, Nature 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. USA, 81:6851-6855 (1984)).

"Humanized" forms of non-human (e.g., murine) antibodies are chimeric immunoglobulins, immunoglobulin chains or fragments thereof (such as Fv, Fab, Fab', F(ab') or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fe), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992). The humanized antibody includes a Primatized antibody wherein the antigen-binding region of the antibody is derived from an antibody produced by immunizing macaque monkeys with the antigen of interest.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatocyte growth factor; fibroblast growth factor; prolactin; placental lactogen; tumor necrosis factor-.alpha. and -.beta.; mullerian-inhibiting substance; mouse gonadotropin-associated peptide; inhibin; activin; vascular endothelial growth factor; integrin; thrombopoietin (TPO); neurotrophic factors or nerve growth factors such as NGF, NT-3, NT4, NT-6, BDNF, CNTF, GDNF, artemin, neurturin, persephin, AL-1 and other eph-receptor family ligands; platelet derived growth factor; transforming growth factors (TGFs) such as TGF-alpha. and TGF-beta.; insulin-like growth factor-I and -II; erythropoietin (EPO); osteoinductive factors; interferons such as interferon-alpha., -beta., and -gamma.; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines. Also included are genetically engineered molecules which regulate cytokine activity such as TrkA-IgG or other soluble receptor chimeras.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

"A polypeptide having biological activity" refers to a polypeptide exhibiting activity similar to, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention).

"Treatment" refers to both therapeutic treatment and prophylactic or preventative measures. Those in need of treatment include those already with the disorder as well as those in which the disorder is to be prevented.

The present invention is based on the discovery of the MANF2, a protein that is a homologous to MANF1 described in patent application WO0119851. The experiments described herein demonstrate that MANF2 molecule is 187 amino acid protein which expressed in all tissues analysed but predominantly in heart, kidney, liver, skeletal muscle, prostate, thymus and several different regions of the brain. In particular, MANF2 protein has been found to be present in a variety of tissues, including neurons, thus indicating that MANF2 agonists can be used to stimulate proliferation, growth, survival, differentiation, metabolism, or regeneration of MANF2 receptor containing cells.

In one embodiment, the invention provides a purified protein comprising, or alternatively consisting of a polypeptide, a biologically active fragment, or an antigenic fragment of MANF2.

In another embodiment the present invention is also directed to proteins which comprise, or alternatively consist of, an amino acid sequence which is at least 80%, 85%, 90%, 95%, 96%, 97%, 98%, 99% or 100%, identical to MANF2 protein.

Due to the degeneracy of the genetic code, one of ordinary skill in the art will immediately recognize that a large number of the nucleic acid molecules having a sequence at least 80%, 85%, 90%, 95%, 96%, 97%, 98%, 99%, or 100% identical to the nucleic acid sequence of the cDNA contained in SEQ ID NO:1 of FIG. 7 or fragments thereof, will encode polypeptides "having functional activity." In fact, since degenerate variants of any of these nucleotide sequences all encode the same polypeptide, in many instances, this will be, clear to the skilled artisan. It will be further recognized in the art that, for such nucleic acid molecules that are not degenerate variants, a reasonable number will also encode a polypeptide having functional activity. This is because the skilled artisan is fully aware of amino acid substitutions that are either less likely or not likely to significantly effect protein function (e.g. replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

In addition to naturally occurring allelic variants of MANF2, changes can be introduced by mutation into MANF2 sequences that incur alterations in the amino acid sequences of the encoded MANF2 polypeptide. Nucleotide substitutions leading to amino acid substitutions at "nonessential" amino acid residues can be made in the sequence of a MANF2 polypeptide. A "non-essential" amino acid residue is a residue that can be altered from the wild-type sequences of MANF2 without altering its biological activity, whereas an "essential" amino acid residue is required for such biological activity. For example, amino acid residues that are conserved among the MANF2 molecules of the invention are predicted to be particularly non-amenable to alteration. Amino acids for which conservative substitutions can be made are well known in the art. Useful conservative substitutions are shown in Table B, "Preferred substitutions." Conservative substitutions whereby an amino acid of one class is replaced with another amino acid of the same type fall within the scope of the subject invention so long as the substitution does not materially alter the biological activity of the compound.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) could be used. See Cunningham et al., Science 244:1081-1085 (1989). The resulting mutant molecules can then be tested for biological activity. Besides conservative amino acid substitutions (See Table B below), variants of the present invention include (i) substitutions with one or more of the non-conserved amino acid residues, where the substituted amino acid residues may or may not be one encoded by the genetic code, or (ii) substitutions with one or more of the amino acid residues having a substituent group, or (iii) fusion of the mature polypeptide with another compound, such as a compound to increase the stability and/or solubility of the polypeptide (for example, 896I polyethylene glycol), or (iv) fusion of the polypeptide with additional amino acids, such as, for example, an IgG Fc fusion peptide, serum albumin (preferably human serum albumin) or a fragment or variant thereof, or leader or secretory sequence, or a sequence facilitating purification. Such variant polypeptides are deemed to be within the scope of those skilled in the art from the teachings herein.

TABLE B

| Preferred substitutions | | |
|---|---|---|
| Original residue | Exemplary substitutions | Preferred substitutions |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

A further embodiment of the invention relates to polypeptides which comprise the amino acid sequence of a polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions from a polypeptide sequence disclosed herein. It is highly preferable for a polypeptide to have an amino acid sequence which comprises the amino acid sequence of a polypeptide, a portion, or a complement of SEQ ID NO:2 of FIG. 7 in order of ever-increasing preference, at least one, but not more than 10, 9, 8, 7, 6, 5, 4, 3, 2 or 1 amino acid substitutions.

In preferred embodiments, the amino acid substitutions are conservative.

In specific embodiments, the polypeptides of the invention comprise, or alternatively, consist of, fragments or variants of a reference amino acid sequence encoded by SEQ ID NO:2 of FIG. 7 wherein the fragments or variants have 1-5, 5-10, 5-25, 5-50, 10-50 or 50-150, amino acid residue additions, substitutions, and/or deletions when compared to the reference amino acid sequence.

In one embodiment techniques suitable for the production of MANF2 polypeptide are well known in the art and include isolating MANF2 from an endogenous source of the polypeptide, peptide synthesis (using a peptide synthesizer) and recombinant techniques (or any combination of these techniques).

In one embodiment, the isolated nucleic acid molecule comprises a nucleotide sequence encoding a protein, wherein the protein comprises an amino acid sequence at least about 45%, preferably 60%, more preferably 70%, 80%, 90%, and most preferably about 95% homologous to that of a MANF2.

In another embodiment, MANF2 polypeptide variants have at least (1) about 80% amino acid sequence identity with a full-length native MANF2 polypeptide sequence shown in SEQ ID NO:2 of FIG. 7, (2) a MANF2 polypeptide sequence lacking the signal peptide, (3) any other fragment of a full-length MANF2 polypeptide sequence. For example, MANF2 polypeptide variants include MANF2 polypeptides wherein one or more amino acid residues are added or deleted at the N- or C-terminus of the full-length native amino acid sequence. A MANF2 polypeptide variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native sequence MANF2 polypeptide sequence. A MANF2 polypeptide variant may have a sequence lacking the signal peptide or any other fragment of a full-length MANF2 polypeptide sequence. Ordinarily, MANF2 variant polypeptides are at least about 10 amino acids in length, often at least about 20 amino acids in length, more often at least about 30, 40, 50, 60, 70, 80, 90, 100 or 150 amino acids in length, or more.

One aspect of the invention provides an isolated nucleic acid molecule comprising, or alternatively consisting of, a polynucleotide having a nucleotide sequence selected from the group consisting of (a) a nucleotide sequence described in SEQ ID NO:1 of FIG. 7 (b) a nucleotide sequence in SEQ ID NO:1 part of which encodes a mature MANF2 polypeptide; (c) a nucleotide sequence which encodes a biologically active fragment of a MANF2; (d) a nucleotide sequence which encodes an antigenic fragment of a MANF2 polypeptide; (e) a nucleotide sequence complementary to any of the nucleotide sequences in (a), (b), (c), (d), above.

The invention further encompasses nucleic acid molecules that differ from the nucleotide sequences due to degeneracy of the genetic code and thus encode the same MANF2 protein as shown in sequence SEQ ID NOs 2 or 4.

In addition sequence polymorphisms that change the amino acid sequences of the MANF2 may exist within a population. For example, allelic variation among individuals will exhibit genetic polymorphism in MANF2. The terms "gene" and "recombinant gene" refer to nucleic acid molecules comprising an open reading frame (ORF) encoding MANF2, preferably a vertebrate MANF2. Such natural allelic variations can typically result in 1-5% variance in MANF2. Any and all such nucleotide variations and resulting amino acid polymorphisms in the MANF2, which are the result of natural allelic variation and that do not alter the functional activity of the MANF2 are within the scope of the invention.

Moreover, MANF2 from other species that have a nucleotide sequence that differs from the human sequence of MANF2 are contemplated. Nucleic acid molecules corresponding to natural allelic variants and homologues of MANF2 cDNAs of the invention can be isolated based on their homology to MANF2 using cDNA-derived probes to hybridize to homologous MANF2 sequences under stringent conditions.

"MANF2 variant polynucleotide" or "MANF2 variant nucleic acid sequence" means a nucleic acid molecule which encodes an active MANF2 that (1) has at least about 80% nucleic acid sequence identity with a nucleotide acid sequence encoding a full-length native MANF2, (2) a full-length native MANF2 lacking the signal peptide, or (3) any other fragment of a full-length MANF2. Ordinarily, a F2 variant polynucleotide will have at least about 80% nucleic acid sequence identity, more preferably at least about 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence encoding a full-length native MANF2. A MANF2 variant polynucleotide may encode full-length native MANF2 lacking the signal peptide with or without the signal sequence, or any other fragment of a full-length MANF2. Variants do not encompass the native nucleotide sequence.

Ordinarily, MANF2 variant polynucleotides are at least about 30 nucleotides in length, often at least about 60, 90, 120, 150, 180, 210, 240, 270, 300, 400 nucleotides in length, more often at least about 500 nucleotides in length, or more.

The structure and sequence of the mammalian MANF2 cDNA sequence which encodes the mouse and human sequences disclosed herein, make it possible to clone gene sequences from other mammals which encode the MANF2. Of particular interest to the present invention is the ability to clone the human MANF2 molecules using the sequences disclosed herein. The DNA encoding MANF2 may be obtained from any cDNA library prepared from tissue believed to possess the MANF2 mRNA and to express it at a detectable level, as shown herein in the Examples. Accordingly, MANF2 DNA can be conveniently obtained from a cDNA library prepared, for example, from mammalian fetal liver, brain, muscle, intestine, and peripheral nerves. The MANF2-encoding gene may also be obtained from a genomic library or by oligonucleotide synthesis.

Libraries are screened with probes (such as antibodies to the MANF2 or oligonucleotides of about 20-80 bases) designed to identify the gene of interest or the protein encoded by it. Screening the cDNA or genomic library with the selected probe may be conducted using standard procedures as described in chapters 10-12 of Sambrook et al., Molecular Cloning: A Laboratory Manual (New York: Cold Spring Harbor Laboratory Press, 1989) or alternatively to use PCR methodology as described in section 14 of Sambrook et al., supra.

Amino acid sequence variants of MANF2 are prepared by introducing appropriate nucleotide changes into the MANF2 DNA, or by synthesis of the desired MANF2 polypeptide. Such variants represent insertions, substitutions, and/or specified deletions of, residues within or at one or both of the ends of the amino acid sequence of a naturally occurring MANF2, such as the MANF2 shown in FIG. 7, SEQ ID Nos. 2 and 4. Preferably, these variants represent insertions and/or substitutions within or at one or both ends of the mature sequence, and/or insertions, substitutions and/or specified deletions within or at one or both of the ends of the signal sequence of the MANF2. Any combination of insertion, substitution, and/or specified deletion is made to arrive at the final construct, provided that the final construct possesses the desired biological activity as defined herein.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

The nucleic acid (e.g., cDNA or genomic DNA) encoding the MANF2 is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The MANF2s of this invention may be produced recombinantly not only directly, but also as a fusion polypeptide with a heterologous polypeptide, which is preferably a signal sequence or other polypeptide having a specific cleavage site at the N-terminus of the mature protein or polypeptide. Fusion proteins can be easily created using recombinant methods. A nucleic acid encoding MANF2 can be fused in-frame with a non-MANF2 encoding nucleic acid, to the MANF2 N- or COOH-terminus, or internally. Fusion genes may also be synthesized by conventional techniques, including automated DNA synthesizers. A MANF2 fusion protein may include any portion to the entire MANF2, including any number of the biologically active portions. Fusion polypeptides are useful in expression studies, cell-localization, bioassays, and MANF2 purification Alternatively, MANF2 fusion protein can also be easily created using PCR amplification and anchor primers that give rise to complementary overhangs between two consecutive gene fragments that can subsequently be annealed and reamplified to generate a chimeric gene sequence (Ausubel et al., supra).

The signal sequence may be a component of the vector, or it may be a part of the MANF2 DNA that is inserted into the vector. The heterologous signal sequence selected preferably is one that is recognized and processed (i.e., cleaved by a signal peptidase) by the host cell. For prokaryotic host cells that do not recognize and process the native MANF2 signal sequence, the signal sequence is substituted by a prokaryotic signal sequence selected, for example, from the group of the alkaline phosphatase, penicillinase, or heat-stable enterotoxin II leaders. For yeast secretion the native signal sequence may be substituted by, e.g., the yeast invertase leader, alpha-factor leader (including *Saccharomyces* and *Kluyveromyces*, alpha-factor leaders, the latter described in U.S. Pat. No. 5,010,182 issued Apr. 23, 1991), or acid phosphatase leader, the *Candida albicans* glucoamylase leader (FP 362,179 published Apr. 4, 1990). In mammalian cell expression the native signal sequence (e.g., the MANF2 presequence that normally directs secretion of MANF2 from human cells in vivo) is satisfactory, although other mammalian signal sequences may be suitable, such as signal sequences from other animal MANF2s, and signal sequences from secreted polypeptides of the same or related species, as well as viral secretory leaders, for example, the herpes simplex gD signal.

Expression and cloning vectors usually contain a promoter that is recognized by the host organism and is operably linked to the MANF2 nucleic acid. Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences. The choice of these elements depends on the organisms in which the vector will be used and are easily determined. Some of these elements may be conditional, such as an inducible or conditional promoter that is turned "on" when conditions are appropriate.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably linked to elements, such as promoters, that signal to the host cell to transcribe the inserted DNA. Some promoters are exceptionally useful, such as inducible promoters that control gene transcription in response to specific factors. Operably linking MANF2 or anti-sense construct to an inducible promoter can control the expression of MANF2 or fragments, or anti-sense constructs. Examples of classic inducible promoters include those that are responsive to a-interferon, heat-shock, heavy metal ions, and steroids such as glucocorticoids (Kaufman R J, Vectors Used for Expression in Mammalian Cells," Methods in Enzymology, Gene Expression Technology, David V. Goeddel, ed., 1990, 185:487-511) and tetracycline. Other desirable inducible promoters include those that are not endogenous to the cells in which the construct is being introduced, but, however, is responsive in those cells when the induction agent is exogenously supplied.

Promoters are untranslated sequences located upstream (5') to the start codon of a structural gene (generally within about 100 to 1000 bp) that control the transcription and translation of particular nucleic acid sequence, such as the MANF2 nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to MANF2-encoding DNA by removing the promoter from the source DNA by restriction enzyme digestion and inserting the isolated promoter sequence into the vector. Both the native MANF2 promoter sequence and many heterologous promoters may be used to direct amplification and/or expression of the MANF2 DNA. However, heterologous promoters are preferred, as they generally permit greater transcription and higher yields of MANF2 as compared to the native MANF2 promoter. Various promoters exist for use with prokaryotic, eukaryotic, yeast and mammalian host cells, known for skilled artisan.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding MANF2.

Construction of suitable vectors containing one or more of the above-listed components employs standard ligation techniques. Isolated plasmids or DNA fragments are cleaved, tailored, and religated in the form desired to generate the plasmids required.

Particularly useful in the practice of this invention are expression vectors that provide for the transient expression in mammalian cells of DNA encoding MANF2. In general, transient expression involves the use of an expression vector that is able to replicate efficiently in a host cell, such that the host cell accumulates many copies of the expression vector and, in turn, synthesizes high levels of a desired polypeptide encoded by the expression vector, Sambrook et al., supra, pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of MANF2 that are biologically active.

Propagation of vertebrate cells in culture (tissue culture) has become a routine procedure. See, e.g., Tissue Culture, Academic Press, Kruse and Patterson, editors (1973). Examples of useful mammalian host cell lines are monkey kidney CV1 line transformed by SV40 (COS-7, ATCC CRL 1651); Chinese hamster ovary cells/−DHFR (CHO, Urlaub et al., Proc. Natl. Acad. Sci. USA, 77:4216 (1980)); human cervical carcinoma cells (HELA, ATCC CCL 2); and canine kidney cells (MDCK, ATCC CCL 34);

Host cells are transfected and preferably transformed with the above-described expression or cloning vectors for MANF2 production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers.

General aspects of mammalian cell host system transformations have been described in U.S. Pat. No. 4,399,216 issued Aug. 16, 1983. Transformations into yeast are typically carried out according to the method of Van Solingen et al., J. Bact., 130:946 (1977) and Hsiao et al., Proc. Natl. Acad. Sci. USA, 76:3829 (1979). However, other methods for introducing DNA into cells, such as by nuclear microinjection, electroporation, bacterial protoplast fusion with intact cells, or polycations, e.g., polybrene, polyomithine, etc., may also be used. For various techniques for transforming mammalian cells, see Keown et al., Methods in Enzymology, 185:527-537 (1990) and Mansour et al., Nature, 336:348-352 (1988).

Prokaryotic cells used to produce the MANF2 polypeptide of this invention are cultured in suitable media as described generally in Sambrook et al., supra. In general, principles, protocols, and practical techniques for maximizing the productivity of mammalian cell cultures can be found in Mammalian Cell Biotechnology: a Practical Approach, M. Butler, ed. (IRL Press, 1991).

Gene amplification and/or expression may be measured in a sample directly, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide or antibodies recognizing specific duplexes, including DNA duplexes, RNA duplexes, and DNA-RNA hybrid duplexes or DNA-protein duplexes.

Gene expression, alternatively, can be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., Am. J. Clin. Path., 75:734-738 (1980).

Recombinant Production

When MANF2 is produced in a recombinant cell other than one of human origin, the MANF2 is completely free of proteins or polypeptides of human origin. However, it is necessary to purify MANF2 from recombinant cell proteins or polypeptides to obtain preparations that are substantially homogeneous as to MANF2. As a first step, the culture medium or lysate can be centrifuged to remove particulate cell debris. MANF2 can then be purified from contaminant soluble proteins and polypeptides with the following procedures, which are exemplary of suitable purification procedures: by fractionation on an ion-exchange column; ethanol precipitation; reverse phase HPLC; chromatography on silica; chromatofocusing; immunoaffinity; epitope-tag binding resin; SDS-PAGE; ammonium sulfate precipitation; gel filtration using, for example, Sephadex G-75; and protein A Sepharose columns to remove contaminants such as IgG.

MANF2 variants in which residues have been deleted, inserted, or substituted are recovered in the same fashion as native sequence MANF2, taking account of any substantial changes in properties occasioned by the variation. Immunoaffinity resins, such as a monoclonal anti-MANF2 resin, can be employed to absorb the MANF2 variant by binding it to at least one remaining epitope.

Variants can be assayed as taught herein. A change in the immunological character of the MANF2 molecule, such as affinity for a given antibody, can be measured by a competitive-type immunoassay. Other potential modifications of protein or polypeptide properties such as redox or thermal stability, hydrophobicity, susceptibility to proteolytic degradation, or the tendency to aggregate with carriers or into multimers are assayed by methods well known in the art.

This invention encompasses chimeric polypeptides comprising MANF2 fused to a heterologous polypeptide. A chimeric MANF2 is one type of MANF2 variant as defined herein. In one preferred embodiment, the chimeric polypeptide comprises a fusion of the MANF2 with a tag polypeptide which provides an epitope to which an anti-tag antibody or molecule can selectively bind. The epitope-tag is generally provided at the amino- or carboxyl-terminus of the MANF2. Such epitope-tagged forms of the MANF2 are desirable, as the presence thereof can be detected using a labeled antibody against the tag polypeptide. Also, provision of the epitope tag enables the MANF2 to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). Other tag polypeptides have been disclosed. Examples include the Flag-peptide (Hopp et al., BioTechnology, 6:1204-1210 (1988)); the KT3 epitope peptide (Martin et al., Science, 255:192-194 (1992)); an alpha-tubulin epitope peptide (Skinner et al., J. Biol. Chem., 266:15163-15166 (1991)); and the T7 gene protein peptide tag (Lutz-Freyermuth et al., Proc. Natl. Acad. Sci. USA, 87:6393-6397 (1990)). Once the tag polypeptide has been selected, an antibody thereto can be generated using the techniques disclosed herein. A C-terminal poly-histidine sequence tag is preferred. Poly-histidine sequences allow isolation of the tagged protein by Ni-NTA chromatography as described (Lindsay et al. Neuron 17:571-574 (1996)), for example.

The general methods suitable for the construction and production of epitope-tagged MANF2 are the same as those disclosed hereinabove.

Epitope-tagged MANF2 can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-tagged MANF2 can be eluted from the affinity column by varying the buffer pH or ionic strength or adding chaotropic agents, for example.

Chimeras constructed from a MANF2 sequence linked to an appropriate immunoglobulin constant domain sequence (immunoadhesins) are known in the art. Immunoadhesins reported in the literature include fusions of the T cell receptor (Gascoigne et al., Proc. Natl. Acad. Sci. USA, 84: 2936-2940 (1987)); CD4* (Capon et al., Nature 337: 525-531 (1989); Traunecker et al., Nature, 339: 68-70 (1989); Zettmeissl et al., DNA Cell Biol USA, 9: 347-353 (1990); Byn et al., Nature, 344: 667-670 (1990)); TNF receptor (Ashkenazi et al., Proc. Natl. Acad. Sci. USA, 88: 10535-10539 (1991); Lesslauer et al., Eur. J. Immununol., 27: 2883-2886 (1991); Peppel et al., J. Exp. Med., 174:1483-1489 (1991)); and IgE receptor alpha* (Ridgway et al., J. Cell. Biol., 1 15:abstr. 1448 (1991)), where the asterisk (*) indicates that the receptor is member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the MANF2-immunoglobulin chimeras of the present invention, nucleic acid encoding the MANF2 will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimise the biological activity, secretion or binding characteristics of the MANF2-immunoglobulin chimeras.

The choice of host cell line for the expression of MANF2 immunoadhesins depends mainly on the expression vector. Another consideration is the amount of protein that is required. Milligram quantities often can be produced by transient transfections utilizing, for example, calcium phosphate or DEAE-dextran method (Aruffo et al., Cell, 61:1303-1313 (1990); Zettmeissl et al., DNA Cell Biol. US, 9:347-353 (1990)). If larger amounts of protein are desired, the immunoadhesin can be expressed after stable transfection of a host cell line, for example, introducing the expression vectors into Chinese hamster ovary (CHO) cells in the presence of an additional plasmid encoding dihydrofolate reductase.

Antibodies

MANF2 nucleic acid is useful for the preparation of MANF2 polypeptide by recombinant techniques exemplified herein which can then be used for production of anti-MANF2 antibodies having various utilities described below.

Antibodies useful for immunohistochemical staining and/or assay of sample fluids may be either monoclonal or polyclonal.

The invention further includes an antibody that specifically binds with MANF2, or a fragment thereof. In a preferred embodiment, the invention includes an antibody that inhibits the biological activity of MANF2. The antibody is useful for the identification for MANF2 in a diagnostic assay for the determination of the levels of MANF2 in a mammal having a disease associated with MANF2 levels. In addition, an antibody that specifically binds MANF2 is useful for blocking the interaction between MANF2 and its receptor, and is therefore useful in a therapeutic setting for treatment of MANF2 related disease, as described herein.

Monoclonal antibodies directed against full length or peptide fragments of a MANF2 protein or peptide may be prepared using any well-known monoclonal antibody preparation procedures, such as those described, for example, in Harlow et al. (1988, In: Antibodies, A Laboratory Manual, Cold Spring Harbor, N.Y.). Anti-MANF2 mAbs may be prepared using hybridoma methods comprising at least four steps: (1) immunizing a host, or lymphocytes from a host; (2) harvesting the mAb secreting (or potentially secreting) lymphocytes, (3) fusing the lymphocytes to immortalized cells, and (4) selecting those cells that secrete the desired (anti-MANF2) mAb. The mAbs may be isolated or purified from the culture medium or ascites fluid by conventional Ig purification procedures such as protein A-Sepharose, hydroxylapatite chromatography, gel electrophoresis, dialysis, ammonium sulfate precipitation or affinity chromatography (Harlow et al, supra).

A mouse, rat, guinea pig, hamster, or other appropriate host is immunized to elicit lymphocytes that produce or are capable of producing Abs that will specifically bind to the immunogen. Alternatively, the lymphocytes may be immunized in vitro.

If human cells are desired, peripheral blood lymphocytes are generally used; however, spleen cells or lymphocytes from other mammalian sources are preferred.

The immunogen typically includes MANF2 or a MANF2 fusion protein.

The invention further comprises humanized and human anti-MANF2 Abs.

Humanized forms of non-human Abs are chimeric Igs, Ig chains or fragments (such as Fv, Fab, Fab', F(ab') or other antigen-binding subsequences of Abs) that contain minimal sequence derived from non-human Ig.

Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody (Jones et al., Nature 321:522-525 (1986); Riechmann et al., Nature 332:323-327 (1988); Verhoeyen et al., Science 239:1534-1536, (1988). Such "humanized" Abs are chimeric Abs (U.S. Pat. No. 4,816,567, 1989), wherein substantially less than an intact human variable domain has been substituted by the corresponding sequence from a non-human species. In practice, humanized Abs are typically human Abs in which some CDR residues and possibly some FR residues are substituted by residues from analogous sites in rodent Abs. Humanized Abs include human Igs (recipient antibody) in which residues from a complementary determining region (CDR) of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized Abs may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region typically that of a human Ig (Jones et al., supra; Presta L G, Curr Opin Biotechnol 3:394-398 (1992).

Human Abs can also be produced using various techniques, including phage display libraries (Hoogenboom et al., Nucleic Acids Res 19:4133-4137 (1991); Marks et al., Biotechnology (NY) 10:779-83 (1991) and the preparation of human mAbs (Boerner et al., J Immunol 147(1):86-95 (1991); Reisfeld and Sell, Monoclonal Antibodies and Cancer Therapy Alan R. Liss, Inc., New York (1985). Similarly, introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire (U.S. Pat. Nos. 5,545,807, 1996; U.S. Pat. No. 5,545,806, 1996; U.S. Pat. No. 5,569,825, 1996; U.S. Pat. No. 5,633,425, 1997; U.S. Pat. No. 5,661,016, 1997; U.S. Pat. No. 5,625,126, 1997; Fishwild et al., Nat Biotechnol 14:845-51 (1996); Lonberg and Huszar, Int Rev Immunol 13:65-93 (1995); Lonberg et al., Nature 368:856-9 (1994); Marks et al., Biotechnology (NY) 10:779-783 (1992)).

In one preferred embodiment the instant inventions also comprises bi-specific mAbs that are monoclonal, preferably human or humanized, that have binding specificities for at least two different antigens. For example, a binding specificity is MANF2; the other is for any antigen of choice, preferably a cell surface protein or receptor or receptor subunit.

Traditionally, the recombinant production of bi-specific Abs is based on the co-expression of two Ig heavy-chain/light-chain pairs, where the two heavy chains have different specificities (Milstein and Cuello, Nature 305:537-540 (1983)). Because of the random assortment of Ig heavy and light chains, the resulting hybridomas (quadromas) produce a potential mixture of ten different antibody molecules, of which only one has the desired bi-specific structure. The desired antibody can be purified using affinity chromatography or other techniques (WO 93/08829, (1993); Traunecker et al., Trends Biotechnol 9:109-113 (1991)).

To manufacture a bi-specific antibody (Suresh et al., Methods Enzymol. 121:210-228 (1986)), variable domains with the desired antibody-antigen combining sites are fused to Ig constant domain sequences. The fusion is preferably with an Ig heavy-chain constant domain, comprising at least part of the hinge, CH2, and CH3 regions. Preferably, the first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

Fab fragments may be directly recovered from E. coli and chemically coupled to form bi-specific Abs. For example, fully humanized bi-specific F(ab') Abs can be produced (Shalaby et al., J Exp Med. 175:217-225 (1992)). Each Fab fragment is separately secreted from E. coli and directly coupled chemically in vitro, forming the bi-specific antibody.

Various techniques for making and isolating bi-specific antibody fragments directly from recombinant cell culture have also been described. For example, leucine zipper motifs can be exploited (Kostelny et al., Immunol. 148:1547-1553 (1992)). Peptides from the Fos and Jun proteins are linked to the Fab portions of two different Abs by gene fusion. The antibody homodimers are reduced at the hinge region to form monomers and then reoxidized to form antibody heterodimers. This method can also produce antibody homodimers.

The "diabody" technology (Holliger et al., Proc Natl Acad Sci USA. 90:6444-6448 (1993)) provides an alternative method to generate bi-specific antibody fragments. The fragments comprise a heavy-chain variable domain (VH) connected to a light-chain variable domain (VL) by a linker that is too short to allow pairing between the two domains on the same chain. The VH and VL domains of one fragment are forced to pair with the complementary VL and VH domains of another fragment, forming two antigen-binding sites. Another strategy for making bi-specific antibody fragments is the use of single-chain Fv (sFv) dimers (Gruber et al., Immunol. 152:5368-5374 (1994)). Abs with more than two valencies are also contemplated, such as tri-specific Abs (Tutt et al., J Immunol. 147:60-69 (1991)).

Polyclonal Abs can be raised in a mammalian host, for example, by one or more injections of an immunogen and, if desired, an adjuvant. Typically, the immunogen and/or adjuvant are injected in the mammal by multiple subcutaneous or intraperitoneal injections. The immunogen may include MANF2 or a MANF2 fusion protein.

Examples of adjuvants include Freund's complete and monophosphoryl Lipid A synthetic-trehalose dicorynomycolate (MPL-TDM). To improve the immune response, an immunogen may be conjugated to a protein that is immunogenic in the MANF2 host, such as keyhole limpet hemocyanin (KLH), serum albumin, bovine thyroglobulin, and soybean trypsin inhibitor. Protocols for antibody production are described by (Harlow et al, supra). Alternatively, pAbs may be made in chickens, producing IgY molecules (Schade et al, The production of avian (egg yolg) antibodies: IgY. The report and recommendations of ECVAM workshop. Alternatives to Laboratory Animals NAILA). 24:925-934 (1996)).

Treatment

The MANF2 protein and MANF2 gene are believed to find ex vivo or in vivo therapeutic use for administration to a mammal, particularly humans, in the treatment of diseases or disorders, related to MANF2 or MANF1 activity or benefited by MANF2/MANF1-responsiveness (see WO0119851). Particularly preferred are neurologic disorders, preferably central nervous system disorders, Parkinson's disease or Alzheimer's disease.

The patient is administered an effective amount of MANF2 protein, peptide fragment, or variant of the invention. Therapeutic methods comprising administering MANF2, MANF2 agonists, MANF2 antagonists or anti-MANF2 antibodies are within the scope of the present invention. The present invention also provides for pharmaceutical compositions comprising MANF2 protein, peptide fragment, or derivative in a suitable pharmacological carrier. The MANF2 protein, peptide fragment, or variant may be administered systemically or locally. Applicable to the methods taught herein, the MANF2 protein can be optionally administered prior to, after, or preferably concomitantly with (or in complex with) MANF1.

A disease or medical disorder is considered to be nerve damage if the survival or function of nerve cells and/or their axonal processes is compromised. Such nerve damage occurs as the result conditions including (a) Physical injury, which causes the degeneration of the axonal processes and/or nerve cell bodies near the site of the injury; (b) Ischemia, as a stroke; (c) Exposure to neurotoxins, such as the cancer and AIDS chemotherapeutic agents such as cisplatin and dideoxycytidine (ddC), respectively; (d) Chronic metabolic diseases, such as diabetes or renal dysfunction; and (e) Neurodegenerative diseases such as Parkinson's disease, Alzheimer's disease, and Amyotrophic Lateral Sclerosis (ALS), which cause the degeneration of specific neuronal populations. Conditions involving nerve damage include Parkinson's disease, Alzheimer's disease, Amyotrophic Lateral Sclerosis, stroke, diabetic polyneuropathy, toxic neuropathy, and physical damage to the nervous system such as that caused by physical injury of the brain and spinal cord or crush or cut injuries to the arm and hand or other parts of the body, including temporary or permanent cessation of blood flow to parts of the nervous system, as in stroke.

It is contemplated that MANF2 may be employed to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to diabetic peripheral neuropathy, distal sensorimotor neuropathy, or autonomic neuropathies such as reduced motility of the gastrointestinal tract or atony of the urinary bladder. Examples of neuropathies associated with systemic disease include post-polio syndrome or AIDS-associated neuropathy; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine. Correspondingly, neurotrimin antagonists would be expected to have utility in diseases characterized by excessive neuronal activity. Alzheimer's Disease is marked by widespread neurodegeneration in the brain including an enhanced loss of the cholinergic neurons that reside in the basal forebrain. The loss of the basal forebrain cholinergic neurons contributes to the cognitive and spatial memory deficits in Alzheimer's diseased patients (Gilmor et al., 1999; Lehericy et al. 1993). Restoring and modulating cholinergic function in Alzheimer's patients is a candidate treatment for the disease (Sramek and Cutler, 1999; Mufson et al., 1998). Other neural cell types may also be involved with the disease.

A patient suffering from Parkinson's disease can be treated at the earliest signs of disease symptoms, such as impaired motor function or impaired cognitive function, in order to halt the progression of neurodegeneration. It is also contemplated that the MANF2 cultured cells are administered to individuals in late stages of disease to slow the progression of the nervous system damage.

It is also contemplated by the invention that administration of the MANF2 product in combination with a neurotherapeutic agent commonly used to treat Parkinson's disease will create a synergism of the two treatments, thereby causing marked improvement in patients receiving the combination therapy as compared to individuals receiving only a single therapy.

Pramipexole (mirapex) and levodopa are effective medications to treat motor symptoms of early Parkinson disease (PD). In vitro studies and animal studies suggest that pramipexole may protect and that levodopa may either protect or damage dopamine neurons. Neuroimaging offers the potential of an objective biomarker of dopamine neuron degeneration in PD patients. Coenzyme Q10, a neurotransmitter that is expressed at low levels in Parkinson's patients, is also used for treatment of PD. Levodopa can be combined with another drug such as carbidopa to aid in relieving the side effects of L-dopa. Other medications used to treat Parkinson's disease, either as solo agents or in combination, are Sinemet, Selegiline, (marketed as Eldepryl) may offer some relief from early Parkinson symptoms. Amantadine (Symmetrel) is an anti-viral drug that also provides an anti-Parkinson effect, and is frequently used to widen the "therapeutic window" for Levodopa when used in combination with Sinemet.

It is contemplated that treatment with MANF2 either before, after or simultaneously with any of the above neurotherapeutics will enhance the effect of the neurotherapeutic agent, thereby reducing the amount of agent required by an individual and reducing unwanted side effects produced by multiple or large doses of neurotherapeutic.

The MANF2 gene is expressed in muscle cells. Accordingly, the present invention provides for methods of treating muscle cell disorders comprising administering to a patient in need of such treatment the compounds of the invention. Muscle cell disorders which may benefit from such treatment include but are not limited to the following progressive muscular dystrophies: Duchenne, Becker, Emery-Dreifuss, Landouzy-Dejerine, scapulohumeral, limb-girdle, Von Graefe-Fuchs, oculopharyngeal, myotonic and congenital. In addition, such molecules may be of use in the treatment of congenital (central core, nemaline, centronuclear and congenital fiber-type disproportion) and acquired (toxic, inflammatory) myopathies. The present invention further provides for a method of treating a muscle cell disorder comprising administering to the patient an effective amount of MANF2 protein or an active portion thereof.

Genetic manipulations to achieve modulation of protein expression or activity is also specifically contemplated. For example, where administration of proteins is contemplated, administration of a gene therapy vector to cause the protein of interest to be produced in vivo is also contemplated. Where inhibition of proteins is contemplated (e.g., through use of antibodies or small molecule inhibitors), inhibition of protein expression in vivo by genetic techniques, such as knock-out techniques or anti-sense therapy, is contemplated.

Any suitable vector may be used to introduce a transgene of interest into an animal. Exemplary vectors that have been described in the literature include replication-deficient retroviral vectors, including but not limited to lentivirus vectors [Kim et al., J. Virol., 72(1): 811-816 (1998); Kingsman & Johnson, Scrip Magazine, October, 1998, pp. 43-46.]; adenoviral (see, for example, U.S. Pat. Nos. 5,824,544; 5,707,618; 5,792,453; 5,693,509; 5,670,488; 5,585,362; Quantin et al., Proc. Natl. Acad. Sci. USA, 89: 2581-2584 (1992); Stratford-Perricadet et al., J. Clin. Invest., 90: 626-630 (1992); and Rosenfeld et al., Cell, 68: 143-155 (1992)), retroviral (see, for example, U.S. Pat. Nos. 5,888,502; 5,830,725; 5,770,414; 5,686,278; 4,861,719), adeno-associated viral (see, for example, U.S. Pat. Nos. 5,474,935; 5,139,941; 5,622,856; 5,658,776; 5,773,289; 5,789,390; 5,834,441; 5,863,541; 5,851,521; 5,252,479; Gnatenko et al., J. Investig. Med., 45: 87-98 (1997), an adenoviral-adenoassociated viral hybrid (see, for example, U.S. Pat. No. 5,856,152) or a vaccinia viral or a herpesviral (see, for example, U.S. Pat. Nos. 5,879,934; 5,849,571; 5,830,727; 5,661,033; 5,328,688); Lipofectin-mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in the entirety. Replication-deficient adenoviral vectors, adeno-associated viral vectors and lentiviruses constitute preferred embodiments.

In embodiments employing a viral vector, preferred polynucleotides include a suitable promoter and polyadenylation sequence to promote expression in the target tissue of interest. For many applications of the present invention, suitable promoters/enhancers for mammalian cell expression include, e.g., cytomegalovirus promoter/enhancer [Lehner et al., J. Clin. Microbiol., 29:2494-2502 (1991); Boshart et al., Cell, 41:521-530 (1985)]; Rous sarcoma virus promoter [Davis et al., Hum. Gene Ther., 4:151 (1993)]; simian virus 40 promoter, long terminal repeat (LTR) of retroviruses, keratin 14 promoter, and α myosin heavy chain promoter.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecrik et al., Proc. Natl. Acad. Sci. USA, 83:41434146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes (Nicolau and Sene, Biochim. Biophys. Acta, 721:185-190 (1982); Fraley, et al., Proc. Natl. Acad Sci. USA, 76:3348-3352 (1979); Felgner, Sci. Am., 276(6):102-6 (1997); Felgner, Hum. Gene Ther., 7(15):1791-3, (1996)), electroporation (Tur-Kaspa, et al., Mol Cell Biol., 6:716-718, (1986); Potter, et al., Proc. Nat. Acad. Sci. USA, 81:7161-7165, (1984)), direct microinjection (Harland and Weintraub, J. Cell Biol., 101: 1094-1099 (1985)), cell fusion, DEAE-dextran (Gopal, Mol Cell Biol., 5:1188-1190 (1985), the calcium phosphate precipitation method (Graham and Van Der Eb, Virology, 52:456-467 (1973); Chen and Okayama, Mol Cell Biol, 7:2745-2752, (1987); Rippe, et al., Mol Cell Biol., 10:689-695 (1990), cell sonication (Fechheimer, et al., Proc. Natl. Acad. Sci. USA, 84:8463-8467 (1987)), gene bombardment using high velocity microprojectiles (Yang, et al., Proc. Natl. Acad. Sci. USA, 87:9568-9572 (1990). The currently preferred in vivo gene transfer techniques include transfection with viral (typically retroviral) vectors and viral coat protein-liposome mediated transfection (Dzau et al., Trends in Biotechnology, 11:205-210 (1993)). In some situations it is desirable to provide the nucleic acid source with an agent that targets the target cells, such as an antibody specific for a cell surface membrane protein or the target cell, a ligand for a receptor on the target cell. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem., 262:4429-4432 (1987); and Wagner et al., Proc. Natl. Acad. Sci. USA, 87:3410-3414 (1990). For review of the currently known gene marking and gene therapy protocols see Anderson et al., Science, 256:808-813 (1992).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat "In Liver Diseases, Targeted Diagnosis And Therapy Using Specific Receptors And Ligands," Wu, G., Wu, C., ed., New York: Marcel Dekker, pp. 87-104 (1991)). The addition of DNA to cationic liposomes causes a topological transition from liposomes to optically birefringent liquid-crystalline condensed globules (Radler, et al., Science, 275(5301):810-4, (1997)). These DNA-lipid complexes are potential non-viral vectors for use in gene therapy and delivery.

Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda, et al., Science, 243:375-378 (1989)). In other embodiments, the liposome may be complexed or employed in conjunction with nuclear nonhistone chromosomal proteins (HMG-1) (Kato, et al., J. Biol. Chem., 266:3361-3364 (1991)). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993), supra).

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., *Proc. Nat. Acad. Sci. USA*, 81:7529-7533 (1984) successfully injected polyomavirus DNA in the form of $CaPO_4$ precipitates into liver and spleen of adult and newborn mice demonstrating active viral replication and acute infection. Benvenisty and Neshif, *Proc. Nat. Acad. Sci. USA*, 83:9551-9555 (1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein, et al., *Nature*, 327:70-73 (1987)). Several devices for accelerating small particles have been developed. One such device relies on a high voltage discharge to generate an electrical current, which in turn provides the motive force (Yang, et al., *Proc. Natl. Acad. Sci. USA*, 87:9568-9572 (1990)). The microprojectiles used have consisted of biologically inert substances such as tungsten or gold beads.

Those of skill in the art are aware of how to apply gene delivery to in vivo and ex vivo situations. For viral vectors, one generally will prepare a viral vector stock. Depending on the type of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various cell types. For practically any cell, tissue or organ type, systemic delivery is contemplated. In other embodiments, a variety of direct, local and regional approaches may be taken. For example, the cell, tissue or organ may be directly injected with the expression vector or protein.

In a different embodiment, ex vivo gene therapy is contemplated. In an ex vivo embodiment, cells from the patient are removed and maintained outside the body for at least some period of time. During this period, a therapy is delivered, after which the cells are reintroduced into the patient.

The invention also provides antagonists of MANF2 activation (e.g., MANF2 antisense nucleic acid, neutralizing antibodies). Administration of MANF2 antagonist to a mammal having increased or excessive levels of endogenous MANF2 activation is contemplated, preferably in the situation where such increased levels of MANF2 lead to a pathological disorder.

Pharmaceutical and Therapeutical Compositions and Formulations

The MANF2 nucleic acid molecules, MANF2 polypeptides, and anti-MANF2 Abs (active compounds) of the invention, and derivatives, fragments, analogs and homologs thereof, can be incorporated into pharmaceutical compositions.

Such compositions of MANF2 are prepared for storage by mixing MANF2 nucleic acid molecule, protein, or antibody having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The MANF2 nucleic acid molecule, protein, or antibodies may also be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

The route of MANF2 nucleic acid molecule, protein, or antibody administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. MANF2 nucleic acid molecule, protein, or antibody is administered continuously by infusion or by bolus injection. Generally, where the disorder permits, one should formulate and dose the MANF2 nucleic acid molecule, protein, or antibody for site-specific delivery. Administration can be continuous or periodic. Administration can be accomplished by a constant- or programmable-flow implantable pump or by periodic injections. The nucleic acid molecules of the invention can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., Proc. Natl. Acad. Sci. USA 91:3054-3057 (1994)). The pharmaceutical preparation of a gene therapy vector can include an acceptable diluent, or can comprise a slow release matrix in which the gene delivery vehicle is imbedded.

Alternatively, where the complete gene delivery vector can be produced intact from recombinant cells, e.g., retroviral vectors, the pharmaceutical preparation can include one or more cells that produce the gene delivery system.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels as described by Langer et al., J. Biomed. Mater. Res., 15:167-277 (1981) and Langer, Chem. Tech., 12:98-105 (1982) or polyvinylalcohol, polylactides (U.S. Pat. No. 3,773,919, EP 58,481), or non-degradable ethylene-vinyl acetate (Langer et al., supra).

Sustained-release MANF2 compositions also include liposomally entrapped MANF2 nucleic acid molecule, protein, or antibodies. Liposomes containing MANF2 nucleic acid molecule, protein, or antibodies are prepared by methods known per se: Epstein et al., Proc. Natl. Acad. Sci. USA, 82:3688-3692 (1985); Hwang et al., Proc. Natl. Acad. Sci. USA, 77:40304034 (1980); EP 52,322; EP 36,676; EP 88,046; EP 143,949; EP 142,641; U.S. Pat. Nos. 4,485,045 and 4,544,545; and EP 102,324. Ordinarily the liposomes are of the small (about 200-800 Angstroms) unilamellar type in which the lipid content is greater than about 30 mol % cholesterol, the selected proportion being adjusted for the optimal MANF2 nucleic acid molecule, protein, or antibody therapy.

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Semipermeable, implantable membrane devices are useful as means for delivering drugs in certain circumstances. For example, cells that secrete soluble MANF2, chimeras or antibodies can be encapsulated, and such devices can be implanted into a patient. For example, into the brain of patients suffering from Parkinson's Disease. See, U.S. Pat. No. 4,892,538 of Aebischer et al.; U.S. Pat. No. 5,011,472 of Aebischer et al.; U.S. Pat. No. 5,106,627 of Aebischer et al.; PCT Application WO 91/10425; PCT Application WO 91/10470; Winn et al., Exper. Neurology, 113:322-329 (1991); Aebischer et al., Exper Neurology, 111:269-275 (1991); and Tresco et al., ASAIO, 38:17-23 (1992).

Accordingly, also included is a method for preventing or treating damage to a nerve or damage to other MANF2-responsive cells, which comprises implanting cells that secrete MANF2, its agonists or antagonists as may be required for the particular condition, into the body of patients in need thereof. Finally, the present invention includes a device for preventing or treating nerve damage or damage to other cells as taught herein by implantation into a patient comprising a semipermeable membrane, and a cell that secretes MANF2 (or its agonists or antagonists as may be required for the particular condition) encapsulated within said membrane and said membrane being permeable to MANF2 (or its agonists or antagonists) and impermeable to factors from the patient detrimental to the cells. The patient's own cells, transformed to produce MANF2 ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished without under experimentation.

The present invention includes, therefore, a method for preventing or treating nerve damage by implanting cells, into the body of a patient in need thereof, cells either selected for their natural ability to generate or engineered to secrete MANF2 or MANF2 antibody. Preferably, the secreted MANF2 or antibody being soluble, human mature MANF2 when the patient is human. The implants are preferably non-immunogenic and/or prevent immunogenic implanted cells from being recognized by the immune system. For CNS delivery, a preferred location for the implant is the cerebral spinal fluid of the spinal cord.

An effective amount of MANF2 nucleic acid molecule, protein, or antibody to be employed therapeutically will depend, for example, upon the therapeutic objectives, the route of administration, and the condition of the patient. Accordingly, it will be necessary for the therapist to titre the dosage and modify the route of administration as required to obtain the optimal therapeutic effect. Typically, the clinician will administer the MANF2 protein or antibody until a dosage is reached that achieves the desired effect. A typical daily dosage for systemic treatment might range from about 1 microgram/kg to up to 10 mg/kg or more, depending on the factors mentioned above. As an alternative general proposition, the MANF2 nucleic acid molecule, protein, or antibody is formulated and delivered to the target site or tissue at a dosage capable of establishing in the tissue a MANF2 level that is efficacious but not unduly toxic. This intra-issue concentration should be maintained if possible by continuous infusion, sustained release, topical application, MANF2-expressing cell implant, or injection at empirically determined frequencies. The progress of this therapy is easily monitored by conventional assays.

The efficacy of virally-delivered or non-virally delivered MANF2 polynucleotides can be tested in any of a number of animal models of the Parkinson's disease, known in the art. For example, the most extensively used animal models of Parkinson's disease replicate the neurodegeneration of dopaminergic neurons usually by administration of toxins. Unilateral injection of 6-hydroxydopamine (6-OHDA) into the substantia nigra of mice or rats results in neuronal loss in the ipsilateral striatum and substantia nigra pars compacta with little change in contralateral hemisphere. Similarly, methamphetamine-induced neurotoxicity results in neurodegeneration of dopaminergic and serotoninergic neurons and is considered by those of skill in the art to be closely aligned to the human condition Efficacy of a therapeutic agent may be evaluated by behavioral outcome using the apomorphine-induced rotational behavior.

Another Parkinson's disease model is constructed using the neurotoxin N-methyl-4-phenyl-1,2,3,6,-tetrahydropyridine (MPTP). MPTP is administered to mammals, such as mice, rats, and monkeys. Administration of MPTP to monkeys results not only in loss of dopaminergic and serotoninergic neurons in substantia nigra pars compacta and striatum, but also in behavioral manifestations similar to those seen in human Parkinson's disease patients, such as akinesia and rigid posture. See, e.g., U.S. Pat. No. 6,362,319, incorporated herein by reference in its entirety.

In contrast to the above-described animal models of Parkinson's disease, a number of inbred strains of mice are available which demonstrate a gradual decline in dopaminergic cell numbers. For example, a D2 receptor-deficient mouse has been generated by homologous recombination whose behavioral characteristics resemble those of patients afflicted with Parkinson's disease. Fitzgerald et al. (1993) Brain Res. 608:247-258. A second example is the weaver mutant mouse which shows a gradual decline in mesenchephalic dopaminergic neuron numbers over time up to 40%. Verina et al.

(1997) Exp. Brain Res. 113:5-12; Adelbrecht et al. (1996) Mol. Brain Res. 43:291-300; Mitsumoto et al. (1994) Science 265:1107-1110.

The present examples used the Sauer and Oertel partial PD model (Sauer and Oertel, Neuroscience (1994) 59:401-415). In this model, intrastriatal injection of 6-OHDA induces progressive retrograde degeneration of DA neurons that starts between 1 to 2 weeks after lesioning and continues over 8 to 16 weeks. This ongoing depletion of DA neurons may be more similar to the disease process of PD and more appropriate as an animal model for therapeutic study than the complete model, which is constructed by destroying the medial forebrain bundle, thereby causing more rapid degeneration of DA neurons. In the experiments detailed below, rats had exhibited consistent behavioral deficits before vector injection. The appearance of apomorphine-induced rotations is generally assumed to represent ~90% depletion of striatal dopamine content (Hudson et al., Brain Res. (1993) 626:167-174). However, studies on PD patients and animal models have indicated that there might be more surviving DA neurons than the levels of dopamine suggested (Javoy-Agid et al., Neuroscience (1990) 38:245-253; Feamley and Lees, Brain (1991) 114:2283-2301; Schulzer et al., Brain (1994) 117:509-516). In the model used herein, the number of CTB-positive neurons on the lesioned side of SN was 28.9% of contralateral value at 4 weeks post-lesion. This is consistent with previous studies using Fluorogold (FG)-retrograde labeling that demonstrated 28.8% (35 days post-lesion) (Kozlowski et al., Exp. Neurol. (2000) 166:1 15) or 34% (4 weeks post-lesion) (Sauer and Oertel, Neuroscience (1994) 59:401-415) of FG-positive cells in the lesioned SN. In addition, most CTB-labeled neurons were TH-positive, suggesting that part of the nigrostriatal projection remained intact at the time of AAV vector injection Without being bound by a particular theory, these remaining portions of intact nigrostriatal projections and DA neurons may serve as substrate for regeneration and functional recovery after MANF2 gene delivery.

Animal models of other neurodegenerative diseases have been described and are useful for evaluating the therapeutic efficacy of virally-delivered MANF2 polynucleotides in the treatment of neurodegenerative disorders in addition to PD. For example, Martin et al. (1995) Brain Res. 683:172-178 describe an animal model of epilepsy, Matheson et al. (1997) NeuroReport 8:1739-1742 and Oppenheim et al. (1995) Nature 373:344-346 describe models of neurodegeneration that results from physical trauma, and Sagot et al. (1996) J. Neurosci. 16:2335-2341 describe a model of motor neuron degeneration in animals.

Diagnostics

The invention also features diagnostic or prognostic kits for use in detecting the presence of MANF2 or allelic variant thereof in a biological sample. The kit provides means for the diagnostics of MANF2 dependent conditions as described hereinabove or for assessing the predisposition of an individual to conditions mediated by variation or dysfunction of MANF2. The kit can comprise a labeled compound capable of detecting MANF2 polypeptide or nucleic acid (e.g. mRNA) in a biological sample. The kit can also comprise nucleic acid primers or probes capable of hybridising specifically to at least of portion of an MANF2 gene or allelic variant thereof. The kit can be packaged in a suitable container and preferably it contains instructions for using the kit.

Purification of Receptor

In yet another aspect of the invention, the MANF2 or MANF2 analog may be used for affinity purification of receptor that binds to the MANF2. MANF2 is a preferred ligand for purification. Briefly, this technique involves: (a) contacting a source of MANF2 receptor with an immobilized MANF2 under conditions whereby the MANF2 receptor to be purified is selectively adsorbed onto the immobilized MANF2; (b) washing the immobilized MANF2 and its support to remove non-adsorbed material; and (c) eluting the MANF2 receptor molecules from the immobilized MANF2 to which they are adsorbed with an elution buffer. In a particularly preferred embodiment of affinity purification, MANF2 is covalently attaching to an inert and porous matrix or resin (e.g., agarose reacted with cyanogen bromide). Especially preferred is a MANF2 immunoadhesin immobilized on a protein-A column. A solution containing MANF2 receptor is then passed through the chromatographic material. The MANF2 receptor adsorbs to the column and is subsequently released by changing the elution conditions (e.g. by changing pH or ionic strength).

The preferred technique for identifying molecules which bind to the MANF2 utilizes a chimeric MANF2 (e.g., epitope-tagged MANF2 or MANF2 immunoadhesin) attached to a solid phase, such as the well of an assay plate. The binding of the candidate molecules, which are optionally labelled (e.g., radiolabeled), to the immobilized MANF2 can be measured. Alternatively, competition for binding of MANF, labelled with I125, can be measured.

Production of Transgenic Animals

Nucleic acids which encode MANF2, preferably from non-human species, such as murine or rat protein, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic, stage. A transgene is a DNA which is integrated into the genome of a cell from which a transgenic animal develops. In one embodiment, the human and/or mouse cDNA encoding MANF2, or an appropriate sequence thereof, can be used to clone genomic DNA encoding MANF2 in accordance with established techniques and the genomic sequences used to generate transgenic animals that contain cells which express DNA encoding MANF2. Methods for generating transgenic animals, particularly animals such as mice, have become conventional in the art and are described, for example, in U.S. Pat. Nos. 4,736,866 and 4,870,009. Typically, particular cells would be targeted for MANF2 transgene incorporation with tissue-specific enhancers, which could result in desired effect of treatment. Transgenic animals that include a copy of a transgene encoding MANF2 introduced into the germ line of the animal at an embryonic stage can be used to examine the effect of increased expression of DNA encoding MANF2. Such animals can be used as tester animals for reagents thought to confer protection from, for example, diseases related to MANF2. In accordance with this facet of the invention, an animal is treated with the reagent and a reduced incidence of the disease, compared to untreated animals bearing the transgene, would indicate a potential therapeutic intervention for the disease.

It is now well-established that transgenes are expressed more efficiently if they contain introns at the 5' end, and if these are the naturally occurring introns (Brinster et al. Proc. Natl. Acad. Sci. USA 85:836-840 (1988); Yokode et al., Science 250:1273-1275 (1990)).

Transgenic offspring are identified by demonstrating incorporation of the microinjected transgene into their genomes, preferably by preparing DNA from short sections of tail and analyzing by Southern blotting for presence of the transgene ("Tail Blots"). A preferred probe is a segment of a transgene fusion construct that is uniquely present in the transgene and not in the mouse genome. Alternatively, substitution of a natural sequence of codons in the transgene with a different sequence that still encodes the same peptide yields a unique region identifiable in DNA and RNA analysis. Transgenic "founder" mice identified in this fashion are bred with normal mice to yield heterozygotes, which are backcrossed to create a line of transgenic mice. Tail blots of each mouse from each generation are examined until the strain is established and homozygous. Each successfully created founder mouse and its strain vary from other strains in the location and copy number of transgenes inserted into the mouse genome, and hence have widely varying levels of transgene expression. Selected animals from each established line are sacrificed at 2 months of age and the expression of the transgene is analyzed by Northern blotting of RNA from liver, muscle, fat, kidney, brain, lung, heart, spleen, gonad, adrenal and intestine.

Production of "Knock Out" Animals

Alternatively, the non-human homologs of MANF2 can be used to construct a MANF2 "knock out" animal, i.e., having a defective or altered gene encoding MANF2, as a result of homologous recombination between the endogenous MANF2 gene and an altered genomic MANF2 DNA introduced into an embryonic cell of the animal. For example, murine MANF2 cDNA can be used to clone genomic MANF2 DNA in accordance with established techniques. A portion of the genomic MANF2 DNA can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, Cell 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., Cell 69:915 (1992)). The selected cells are then injected into a blastocyst of an animal (e.g., a mouse) to form aggregation chimeras (see e.g., Bradley, in Teratocarcinomas and Embryonic Stem Cells: A Practical Approach, E. J. Robertson, ed. (IRL, Oxford, 1987), pp. 113-152). A chimeric embryo can then be implanted into a suitable pseudopregnant female foster animal and the embryo brought to term to create a "knock out" animal. Progeny harbouring the homologously recombined DNA in their germ cells can be identified by standard techniques and used to breed animals in which all cells of the animal contain the homologously recombined DNA. Knockout animals can be characterized for their ability to mimic human neurological disorders and defects.

Equivalents

Although particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims.

Having generally described the invention, the same will be more readily understood by reference to the following examples, which are provided by way of illustration and are not intended as limiting.

EXAMPLES

Example 1

Cloning of MANF2 cDNAs and Expression Analyses of MANF2 mRNA by RT-PCR

We were able to clone full-length mouse and human cDNAs by RT-PCR from mouse (by using primers m-MANF2-ATG and m-MANF2-STOP-del) and human (by using primers h-MANF2-ATG and h-MANF2-STOP-del) brain cells. Mouse total RNA was isolated using RNA extraction kit (Ambion), human RNAs were obtained from Clontech. First strand cDNAs were synthesized with reverse transcriptase (Superscript$^{II}$, Invitrogen) using oligo(dT) (Promega) primed total RNA (5 µg) or poly(A)+ RNA (1 µg) from different tissues as a template.

The primers used in cloning and expression analyses of mouse MANF2 (m-MANF2) and human MANF2 (H-MANF2) were:

```
m-MANF2-ATG
                                   (SEQ ID NO: 5)
ACC ATG CGG TGC ATC AGT CCA ACT GC m-MANF2-int-as
                                   (SEQ ID NO: 6)
CTC ATG GGA CGA GTG ACT TCT CC m-MANF2-STOP
                                   (SEQ ID NO: 7)
GTC AGA GCT CCG TTT GGG GGT ATA TC m-MAEF2-STOP-del
                                   (SEQ ID NO: 8)
GAG CTC CGT TTG GGG GTA TAT C h-MANF2-ATG
                                   (SEQ ID NO: 9)
ACC ATG TGG TGC GCG AGC CCA GTT GC h-MANF2-int-as
                                   (SEQ ID NO: 10)
GCA CAC TCA TTG GGC GAG TGA CTT C h-MANF2-stop
                                   (SEQ ID NO: 11)
GAT CAG AGC TCT GTT TTG GGG TGT GTC h-MANF2-stop-del
                                   (SEQ ID NO: 12)
GAG CTC TGT TTT GGG GTG TGT C
```

PCR reactions were performed in the volume of 25 µl containing 1/10 of RT reaction as a template and 0.25 units of thermostable DNA polymerase (Dynazyme, Finnzymes Ltd), the Expand™ Long Distance or GC-rich PCR System kit (Roche) according to manufacturer's instructions. DNA was amplified using the following conditions: 94° C. (2 minutes); 35 cycles of 94° C. (40 s), 55° C. (40 s), 72° C. (60 s). For all combinations of primers the annealing temperature was 55° C. and the number of cycles was 30-35. The amplified RT-PCR products were resolved on 1.5% agarose gel, cloned into pCRII and pcDNA3-His-V5 vectors (Invitrogen) and verified by sequencing.

Example 2

Cell Culture

Cos-7 and cells were grown in Dulbecco's modified Eagle's medium (DMEM) containing 10% fetal bovine serum (Gibco). Cells were transfected with pcDNA3.1 (Invitrogen) expression vector containing human or mouse MANF2 full length cDNA by using Fugene 6 (Roche) transfection protocol. After 12 h the media was removed and replaced with serum-free DMEM. Cells were harvested 48 hr later and protein extracts were made from cells. Secreted proteins (medium) were concentrated. Protein extracts were resolved on polyacrylamide gel and analyzed by Western blot using V5 antibodies (Invitrogen).

Example 3

In situ hybridization. mouse MANF2 full-length cDNA in pCRII vector was linearized before synthesizing RNA probe. Single-stranded RNA probes were transcribed in vitro using 50 μCi [$^{35}$S]-UTP and T3 or T7 polymerases. After DNAse digestion, probes were precipitated and resuspended in 50% formamide, 10 mM DTT. Sagittal and coronal sections of mouse brains were cut on a cryostat and transferred onto subbed slides. The sections were dried, fixed in 4% paraformaldehyde and hybridized in a buffer containing 50% formamide, 0.3 M NaCl, 10 mM Tris, 10 mM Na PO4 (pH 6.8), 5 mM EDTA, 1×Denhardt's solution, 10% dextran sulphate, 10 mM DTT, 1 mg/ml tRNA, and specific probe). Hybridization were done overnight at 50° C. Washing was done in 50% formamide, 2×SSC at 37° C. followed by RNAse digestion. The slides were exposed to X-ray film or dipped in Kodak NTB-2 emulsion and developed after 14-30 days.

Example 4

Analysis of MANF2 Expression by In Situ Hybridization Probes

Full-length MANF2 cDNA cloned into pCRII-TOPO TA-vector (Invitrogen) was used to prepare antisense and control-sense cRNA probes. Plasmid was linearized with appropriate enzymes, and $^{35}$S-labelled probes were generated by in vitro transcription using $^{35}$S-labelled UTP (Amersham) and SP6 or T7 transcription system (Promega). Unincorporated nucleotides were removed by gel filtration with Sephadex G-50 (NICK column, Pharmacia Biotech). Probes were ethanol-precipitated and dissolved into hybridization buffer (60% deionized formamide (FA), 0.3M NaCl, 20 mM Tris-HCl pH8.0, 5 mM EDTA, 10% dextransulphate, 1×Denhardt solution, 100 mM dithioteritol, 0.5 mg/ml yeast tRNA) to a final concentration 32,000-36,000 cpm/μl.

Tissue Samples

Postnatal NMRI mice brain (P1, P5, P10 and adult) were mounted in Tissuetek on dry ice, and stored at −70 C. Coronal sections from frozen tissue were cut in a cryostat. Mouse embryos (E11, E12, E15) and adult mice testes were fixed in 4% paraformaldehyde (PFA) overnight at 4° C., dehydrated through ethanol series, cleared with toluene, and embedded in paraffin. Sagittal sections were cut and adhered onto silanized glass slides.

In Situ Hybridizations

Cryosections (thawed and air-dried) were fixed in 4% PFA at RT for 15 min, rinsed with PBS and treated with proteinase K (1 μg/ml, Sigma), rinsed, and re-fixed with 4% PFA. After rinsing with PBS, sections were incubated in 50% FA, 2×SSC for 10 min, rinsed with water, acetylated and immersed in 50% FA, 2×SSC for 10 min. Sections were prehybridized with hybridization buffer at 52° C. for 1.5-2 h, and hybridized with the probe (120-150 μl) overnight at 52° C.

Paraffin sections were deparaffinized in xylene, rehydrated through descending series of ethanol (absolute, 94%, 70%, 50%, and 30% ethanol) and fixed in 4% PFA. Slides were washed with PBS, treated with proteinase K (20 μg/ml, Sigma), rinsed with PBS and re-fixed with 4% PFA. For acetylation, sections were placed in 0.1M triethanolamine, pH8.0, and acetic anhydride (2.5 ml/L) was added. After 10 min incubation, slides were rinsed with PBS, dehydrated in ascending series of ethanol and air dried. Probe (120-150 μl) was applied on each slide, and hybridization was performed overnight at 52° C. in a moist chamber.

After hybridization, sections were washed with 10 mM DTT in 5×SSC at 50° C. for 30 min, and in 2×SSC, 30 mM DTT, 50% FA at 55° C. for 30 min (low stringency wash), rinsed three times in NTE-buffer (0.5M NaCl, 5 mM EDTA, 10 mM Tris, pH8.0) at 37° C. for 10 min, treated with ribonuclease A (20 μg/ml) for 30 min and rinsed. A second low stringency wash was performed, and sections were rinsed in 2×SSC and 0.1×SSC for 15 min each, dehydrated through ethanol series (0.3M ammonium acetate in 30%, 60%, 80%, 95% ethanol, absolute ethanol), air dried and exposed on a x-ray film for 5-6 days. Slides were dipped in to NTB-2 emulsion (Kodak), exposed to 5-6 weeks and developed. Sections were counterstained with hematoxylin and mounted in Permount.

Example 5

Production of Recombinant MANF2 Protein in Sf9 Insect Cells

Human MANF2 cDNA was cloned without a putative signal sequence in to pMIB/V5-His expression vector (Insect-Select system, Invitrogen), in frame with N-terminal honeybee mellittin secretion signal and C-terminal V5-6×His tag. Sf9 cells grown in SF-900 II medium (Gibco) with antibiotic-antimycotic (Gibco) were plated in a six well plate ($9 \times 10^5$ cells/well) and when attached, transfected with 2 μg of plasmid using 6 μl of Cellfectin reagent (Invitrogen). After 48 h at 28° C., cells were split 1:5, attached overnight, and blasticidin S (50 μg/ml, Invitrogen) was added. Resistant colonies were grown to confluency to form a polyclonal cell line (Sf9-hMANF2). Stable cells were maintained at 10 μg/ml blasticidin. Secretion of recombinant MANF2 to the culture media was verified by western blotting with mouse monoclonal anti-V5 antibody (1:5000, Invitrogen).

A suspension culture of Sf9-hMANF2 cells was started with logarithmic phase adherent cells. Cells were seeded at $1 \times 10^6$ cells/ml in SF-900 II medium with 10 μg/ml gentamycin and 10 μg/ml blasticidin S. Culture was grown at 28° C. at 120 rpm, and subcultured when density reached about $2 \times 10^6$ cells/ml to maintain logarithmic growth.

Purification of MANF2 Protein from Culture Media

For protein production, Sf9-hMANF2 suspension cultures (vol. 250 ml) were grown for 4-6 days to post-logarithmic phase. Cells were removed by centrifugation at 1200 rpm for 10 min, and MANF2 was purified from IL of clarified media at 4° C.

Step 1. Nickel-Sepharose Purification by Centrifugation

To adjust binding conditions for His-tagged proteins, media was diluted (1:2) with PBS, and imidazole (Sigma) was added to 5 mM final concentration. Chelating Sepharose Fast Flow (Pharmacia Biotech) was charged with 0.1M NiCl$_2$, washed, and resuspended in one gel volume of PBS. For 50 ml of media, 1 ml of Ni-sepharose slurry was added and the sample was kept end-over-end rotation at 4° C. for 1 hour. The gel was sedimented by centrifugation at 500×g for 2 min and washed four times with 0.5M KCl, 5 mM imidazole in PBS. Proteins were eluted with 0.5M imidazole in PBS, pH7.4, using a volume equal to gel volume. Eluates were combined and concentrated with YM-10 Centricon filter devices (Millipore) to a final volume of 50-100 ul. Aliquots were run on SDS-PAGE in 15% gel, and visualized with Coomassie stain.

Step 2. HiTrap Chelating HP column (5 ml, Pharmacia Biotech) was charged with nickel and equilibrated in binding buffer (20 mM sodium phosphate pH7.4). Sample from step 1 was diluted into 5 ml binding buffer and applied on the column. Elution was performed with 0.5M imidazole, 0.5M NaCl in 20 mM sodium phosphate buffer, pH7.4, using linear gradient (0-100%) at flow rate 0.8 ml/min. Fractions (1 ml) were collected and analyzed by western blotting with anti-V5 antibody. Fractions containing MANF2 were concentrated with YM-10 filters to 100 µl. PBS (1 ml) was added, and sample was further concentrated to a final volume of 50 µl.

Example 6

N-Terminal Sequencing and Mass Analysis of Recombinant Human MANF2 Proteins

COS-7 cells were plated on three 9 cm plates and transfected with 10 µg hMANF2-pcDNA3.1 with Fugene 6 reagent (Roche). After 24 h, the media was replaced with serum-free DMEM and cells were incubated for additional 48 h. Culture media (24 ml) was collected and recombinant MANF2 purified as in purification step 1 (see above).

From step 1, 250 µl of elute (total volume 500 µl) was used to reversed phase chromatography. Sample was applied on a C1 column (1 mm×20 mm, Pharmacia Biotech) in 0.1% trifluoroacteic acid (TFA) solution, and eluted with 0-100% acetonitrile gradient in 0.1% TFA. A separate peak containing 3 µg MANF2 was collected, run on 12% SDS-PAGE gel and blotted on a PVDF membrane. The blot was stained, a band containing MANF2 was excised, extracted and applied to N-terminal sequencing.

Molecular mass of recombinant human MANF2 was determined by Q-TOF electrospray analysis. Part of the sample was digested to peptide fragments and fragment masses were determined by Q-TOF.

N-terminal sequencing of recombinant human MANF2 produced in COS-7 cells failed, apparently because N-terminal glutamine (Q) in the predicted sequence of mature protein (QEAGG . . . ) was modified to cyclic pyroglutaminic acid. Mass analysis of MANF2 peptide fragments verified that the signal sequence was cleaved between amino acids at position 26 and 27. Protein was determined to contain 3 or 4 cysteine bridges.

MANF2 from Sf9-hMANF2 stable cell line was analyzed equal manner. N-terminal sequence recombinant protein was determined to be correct. Based on mass analysis, the eight conserved cysteines form four cysteine bridges in the mature protein.

Example 7

Biological Activity of Recombinant MANF2 Proteins
Dopamine Neuron Cultures

For dopamine neuron preparations, midbrain floors from E14 rats or E13 mice were dissected. Tissue was digested with 0.5% trypsin in HBSS for 20 min at 37° C. Trypsin activity was blocked by adding fetal calf serum (FCS). DnaseI (1 mg/ml) was added, and sample was triturated with siliconized glass pipette. Cells were washed twice with complete medium (DMEM-F12 containing 10% HC-3, 0.6% glucose (Sigma) and 1× Glutamax I (Gibco)), and plated on poly-L-ornithine/laminin coated coverslips at density of 150.000 cells per coverslip. On the following day, protein factors were added and cells were cultured for 6 days. Cultures were fixed with 4% PFA in PBS for 10 min at RT washed three times with PBS, postfixed with ice-cold acetone for 15 min at −20° C. and washed. Fixed cultures were blocked with 10% HS in PBS for 1 hour at RT, and sheep anti-tyrosine hydroxylase (TH) antibody (1:200, Chemicon International) was applied for overnight at 4° C. Cultures were washed three times with PBS and secondary antibody Cy3-anti-sheep was applied (1:500) for 45 min at RT. Cultures were washed and mounted in mounting media.

Dorsal Root Ganglion Neuron Cultures

For DRG neuron preparations, tissue from E16 mice was digested with 1% trypsin in HBSS for 45 min at 37° C. Tissue was treated as for dopamine cultures, and isolated cells were plated in complete medium (Ham's F14 medium with SATO). Cells were cultured with or without protein factors for 6 days and counted.

Example 8

Experimental Design

All rats were exposed to a stereotaxic microinfusion twice; first they were given either vehicle (4 µl), MANF2 (10 µg) or GDNF (10 µg), and 6 hours later each animal received 6-OHDA (8 µg) to the same site in left dorsal Striatum. The coordinates in the left striatum relative to the bregma and dura were A/P+1.0, L/M+2.7, D/V −4 according to the atlas of Paxinos and Watson (Paxinos and Watson, 1997, The rat brain in stereotaxic coordinates, Academic press, San Diego). The study consisted of following groups: intrastriatal PBS+6-OHDA, intrastriatal GDNF+6-OHDA and intrastriatal MANF2+6-OHDA.

Rotational Behavior

Behavioral tests were carried out 2 and 4 weeks postlesion. The rats were allowed to habituate to the test chamber for 30 min before D-amphetamine (University Pharmacy, Helsinki, Finland; 2.5 mg/kg i.p) was administrated. The number of full (360°) ipsilateral and contralateral turns was recorded for a period of 2 h. Net ipsilateral turns to the lesion were calculated by subtracting the turns to the left from the turns to the right.

Immunohistochemistry

At 4 weeks postlesion, the rats were anesthetized with an overdose of natriumpentobarbital (90 mg/kg, i.p, Orion Pharma, Finland) and perfused intracardially with phosphate-buffered saline (PBS) followed by 4% paraformaldehyde in 0.1 M sodium phosphate buffer, pH 7.4. The brains were removed, postfixed for 4 h and stored in sodium phosphate buffer containing 20% sucrose at 4° C. Serial coronal cryo-sections of 40 µm were cut on a sliding microtome. Six sets of sections were collected in cryoprotectant solution (0.5M PB, 30% glycerol and 30% ethylenglycole) and stored at −20° C. until immunohistochemical processing. Free-floating sections were processed for TH-immunohistochemistry. Following three rinses in PBS, endogenous peroxidase activity was quenched for 5 minutes in 3% $H_2O_2$/10% methanol/PBS. After 3 rinses in PBS, sections were preincubated with normal horse serum (NHS)/0.3% Triton X-100 in PBS in order to block nonspecific staining. Thereafter sections were incubated overnight at room temperature with 1:2000 dilution of biotinylated mouse-anti-TH (Chemicon, Temecula, Calif.). This was followed by incubations with 1:200 dilution of biotinylated horse-anti-mouse (Vector, BA2001) and by incubation in the avidin-biotin peroxidase complex using the Elite ABC Vectastain kit (Vector Laboratories). The reactions were visualized using DAB as a chromogen.

Morphological Analysis

SN Cell Counts

Unbiased stereological cell counting procedures were used to count TH-positive cells in the substantia nigra pars compacta (SNpc) by using the optical fractionator method in combination with the dissector principle and unbiased counting rules (West et al., 1991, Anat. Rec. 231, 482-497; Mouton et al., 2002, Brain Res. 956, 30-35). The entire SNpc was analyzed with Stereo Investigator platform (MicroBrightField, Germany) attached to Olympus BX51 microscope. From each animal, 3 sections from the central portion of the SNpc, where the medial terminal nucleus (MTN) was present (level A/P −5.3), were selected for quantitative analysis. Optical fractionator estimation method was optimized to give coefficient of error less than x% per individual brain sample. Each reference space was outlined at low power (4×), and cells were counted using a high magnification (60×, oil immersion) objective.

Results

In male Wistar rats a single injection of MANF2 (10 µg) into Striatum was able to prevent the 6-hydroxydopamine (6-OHDA, 8 µg) induced degeneration of dopaminergic nerves of the Nigro-Striatal tract. Under anesthesia, the rats were exposed to a stereotaxic microinjection twice; first they were given either vehicle (PBS, 4 µl, control group) or MANF2 (10 µg, treatment group) and 6 hours later each animal received 6-OHDA (8 µg) to the same site in left dorsal Striatum. The coordinates in the left striatum relative to the bregma and dura were A/P +1.0, L/M +2.7, D/V −4 according to the atlas of Paxinos and Watson (Paxinos and Watson, 1997, The rat brain in stereotaxic coordinates, Academic press, San Diego).

Behavioral tests were carried out twice in all rats. Two and 4 weeks post lesion each rat was given D-amphetamine (2.5 mg/kg, i.p.) in order to induce ipsilateral (to the side of lesion) turning behavior, which was recorded for a period of 2 h. At two weeks post lesion amphetamine (2.5 mg/kg, i.p.) induced significant ipsilateral turning behavior in the control group. On the contrary, no increase in ipsilateral turns was observed in the treatment group (treated with MANF2 prior to 6OHDA). At four weeks post-lesion MANF2 was able to significantly reverse the amphetamine induced ipsilateral turning, and the immunohistochemical analysis showed significant protection of DAergic cells by the neurotrophic factor. Results from the behavioral tests are shown in FIG. 16.

TH-immunohistochemistry. At 4 weeks post lesion, following the second behavioral experiment, the rats were anesthetized with an overdose of sodium pentobarbital (90 mg/kg) and perfused intracardially with phosphate-buffered saline (PBS) followed by 4% paraformaldehyde in 0.1 M sodium phosphate buffer, pH 7.4. Free-floating sections were processed for TH-immunohistochemistry. Unbiased stereological cell counting procedures were used to count TH-positive cells in the substantia nigra pars compacta (SNpc) by using the optical fractionator method in combination with the dissector principle and unbiased counting rules (West et al. 1991, Anat. Rec. 231, 482-497; Mouton et al. 2002, Brain Res. 956, 30-35). The entire SNpc was analyzed with Stereo Investigator platform (MicroBrightField, Germany) attached to Olympus BX51 microscope. The loss of TH-positive cells in Substantia Nigra pars compacta of control group and treatment group was 30% and 4%, respectively. A graphic presentation of the results is shown in FIG. 17.

Retrograde transport of MANF2 from dorsal Striatum to Substantia nigra was observed in male Wistar rats. Iodinated MANF2 was injected by means of stereotaxic injection to dorsal Striatum. Twenty four hours later the rats were anesthetized with an overdose of sodium pentobarbital (90 mg/kg) and perfused intracardially with phosphate-buffered saline (PBS) followed by 4% paraformaldehyde in 0.1 M sodium phosphate buffer, pH 7.4. The brain was removed and it was sliced in 1 mm thick coronal sections. Three millimeter in diameter punctures were taken from dorsal Striatum, Frontal cortex, Hippocampus and Subtantia Nigra. Radioactivity in the punctures was measured by gamma counter (Perkin Elmer). Some of the brains were cut in 40 mM coronal sections and the slices were placed to autoradiography on x-ray film.

Discussion

In Parkinson's disease, which is an age-related neurodegenerative disorder, dopaminergic neurons of the substantia nigra are gradually lost. Neurotrophic factors have a significant therapeutic potential in the treatment of degenerative brain diseases. Neurotrophic factors that could slow or reverse the progression of neuronal degeneration, or enhance the recovery from nerve injury are potential target molecules for drug development. The glial cell line-derived neurotrophic factor (GDNF) is the most potent target-derived trophic factor for dopaminergic neurons described so far (Lin et al., 1993, Science 260, 1130-2). GDNF delivery into the putamen of human Parkinson patients resulted in clinical improvements (Gill et al., 2003, Nat. Med. 9, 589-95), but more recent data from Amgen indicate a serious risk for side effects. This warrants the search for novel neurotrophic factors for the treatment of neurodegenerative diseases.

Our findings indicate that MANF2 is possibly the first evolutionarily conserved neurotrophic factor. MANF2 can as efficiently and possibly more selectively than GDNF rescue midbrain dopaminergic neurons in vivo in a rat 6-OHDA model of Parkinson's disease. A single injection of MANF2 six hours before 6-OHDA delivery into the dorsal striatum of adult rats significantly reduced the amphetamine-induced ipsilateral turning behavior at 2 and 4 weeks post-lesion (see FIG. 16), and almost completely rescued tyrosine hydroxylase positive cells in the substantia nigra (FIG. 17).

MANF2 has a great potential as a therapeutic protein or as a basis for the development of drugs for treatment of Parkinson's disease. MANF2 is also a useful effector of several central neurons and can be considered as the drug for several neurodegenerative disorders and neurological and psychiatric diseases.

What is claimed:

1. A method for treating Parkinson's disease in a patient, comprising:
    directly administering to the brain of the patient a pharmaceutically effective amount of a pharmaceutical composition comprising an adenoviral, an adeno-associated viral or a lentiviral vector comprising an expression control sequence operably linked to the MANF2 nucleic acid sequence encoding the MANF2 polypeptide of SEQ ID NO:2 or the mature MANF2 polypeptide consisting of amino acids 27-187 of SEQ ID NO:2.

2. The method according to claim 1, wherein the vector comprises the MANF2 nucleic acid sequence of SEQ ID NO: 1.

* * * * *

SEQUENCE LISTING

<160> NUMBER OF SEQ ID NOS: 22

<210> SEQ ID NO 1
<211> LENGTH: 564
<212> TYPE: DNA
<213> ORGANISM: Homo sapiens

```
<220> FEATURE:
<221> NAME/KEY: CDS
<222> LOCATION: (1)..(564)

<400> SEQUENCE: 1 atg tgg tgc gcg agc cca gtt gct gtg gtg gcc ttt tgc gcc ggg ctt      48
Met Trp Cys Ala Ser Pro Val Ala Val Val Ala Phe Cys Ala Gly Leu
 1               5                  10                  15 ttg gtc tct cac ccg gtg ctg acg cag ggc cag gag gcc ggg ggg cgg      96
Leu Val Ser His Pro Val Leu Thr Gln Gly Gln Glu Ala Gly Gly Arg
             20                  25                  30 cca ggg gcc gac tgt gaa gta tgt aaa gaa ttc ttg aac cga ttc tac     144
Pro Gly Ala Asp Cys Glu Val Cys Lys Glu Phe Leu Asn Arg Phe Tyr
         35                  40                  45 aag tca ctg ata gac aga gga gtt aac ttt tcg ctg gac act ata gag     192
Lys Ser Leu Ile Asp Arg Gly Val Asn Phe Ser Leu Asp Thr Ile Glu
     50                  55                  60 aaa gaa ttg atc agt ttt tgc ttg gac acc aaa gga aaa gaa aac cgc     240
Lys Glu Leu Ile Ser Phe Cys Leu Asp Thr Lys Gly Lys Glu Asn Arg
 65                  70                  75                  80 ctg tgc tat tat cta gga gcc aca aaa gac gca gcc aca aag atc cta     288
Leu Cys Tyr Tyr Leu Gly Ala Thr Lys Asp Ala Ala Thr Lys Ile Leu
                 85                  90                  95 agt gaa gtc act cgc cca atg agt gtg cat atg cct gca atg aag att     336
Ser Glu Val Thr Arg Pro Met Ser Val His Met Pro Ala Met Lys Ile
            100                 105                 110 tgt gag aag ctg aag aag ttg gat agc cag atc tgt gag ctg aaa tat     384
Cys Glu Lys Leu Lys Lys Leu Asp Ser Gln Ile Cys Glu Leu Lys Tyr
        115                 120                 125 gaa aaa aca ctg gac ttg gca tca gtt gac ctg cgg aag atg aga gtg     432
Glu Lys Thr Leu Asp Leu Ala Ser Val Asp Leu Arg Lys Met Arg Val
    130                 135                 140 gca gag ctg aag cag atc ctg cat agc tgg ggg gag gag tgc agg gcc     480
Ala Glu Leu Lys Gln Ile Leu His Ser Trp Gly Glu Glu Cys Arg Ala
145                 150                 155                 160 tgt gca gaa aaa act gac tat gtg aat ctc att caa gag ctg gcc ccc     528
Cys Ala Glu Lys Thr Asp Tyr Val Asn Leu Ile Gln Glu Leu Ala Pro
                165                 170                 175 aag tat gca gcg aca cac ccc aaa aca gag ctc tga                     564
Lys Tyr Ala Ala Thr His Pro Lys Thr Glu Leu
                180                 185

<210> SEQ ID NO 2
<211> LENGTH: 187
<212> TYPE: PRT
<213> ORGANISM: Homo sapiens

<400> SEQUENCE: 2

Met Trp Cys Ala Ser Pro Val Ala Val Val Ala Phe Cys Ala Gly Leu
 1               5                  10                  15

Leu Val Ser His Pro Val Leu Thr Gln Gly Gln Glu Ala Gly Gly Arg
             20                  25                  30

Pro Gly Ala Asp Cys Glu Val Cys Lys Glu Phe Leu Asn Arg Phe Tyr
         35                  40                  45

Lys Ser Leu Ile Asp Arg Gly Val Asn Phe Ser Leu Asp Thr Ile Glu
     50                  55                  60

Lys Glu Leu Ile Ser Phe Cys Leu Asp Thr Lys Gly Lys Glu Asn Arg
 65                  70                  75                  80

Leu Cys Tyr Tyr Leu Gly Ala Thr Lys Asp Ala Ala Thr Lys Ile Leu
                 85                  90                  95
```

```
Ser Glu Val Thr Arg Pro Met Ser Val His Met Pro Ala Met Lys Ile
            100                 105                 110

Cys Glu Lys Leu Lys Lys Leu Asp Ser Gln Ile Cys Glu Leu Lys Tyr
        115                 120                 125

Glu Lys Thr Leu Asp Leu Ala Ser Val Asp Leu Arg Lys Met Arg Val
    130                 135                 140

Ala Glu Leu Lys Gln Ile Leu His Ser Trp Gly Glu Glu Cys Arg Ala
145                 150                 155                 160

Cys Ala Glu Lys Thr Asp Tyr Val Asn Leu Ile Gln Glu Leu Ala Pro
                165                 170                 175

Lys Tyr Ala Ala Thr His Pro Lys Thr Glu Leu
            180                 185

<210> SEQ ID NO 3
<211> LENGTH: 564
<212> TYPE: DNA
<213> ORGANISM: Mus musculus
<220> FEATURE:
<221> NAME/KEY: CDS
<222> LOCATION: (1)..(564)

<400> SEQUENCE: 3 atg cgg tgc atc agt cca act gct ctg gtg acc ttt tgc gcc ggg ttt    48
Met Arg Cys Ile Ser Pro Thr Ala Leu Val Thr Phe Cys Ala Gly Phe
1               5                   10                  15 tgt atc tcg aac cct gtg ctg gcg cag ggc ctg gag gcc ggt gtg ggg    96
Cys Ile Ser Asn Pro Val Leu Ala Gln Gly Leu Glu Ala Gly Val Gly
                20                  25                  30 ccg agg gct gac tgt gaa gta tgt aaa gaa ttc tta gac cga ttc tac    144
Pro Arg Ala Asp Cys Glu Val Cys Lys Glu Phe Leu Asp Arg Phe Tyr
            35                  40                  45 aac tcc ctg cta agc aga ggc ata gac ttt tct gcg gac acc ata gag    192
Asn Ser Leu Leu Ser Arg Gly Ile Asp Phe Ser Ala Asp Thr Ile Glu
        50                  55                  60 aaa gag ctg ctc aac ttt tgc tca gat gcc aaa gga aaa gaa aac cgc    240
Lys Glu Leu Leu Asn Phe Cys Ser Asp Ala Lys Gly Lys Glu Asn Arg
65                  70                  75                  80 ctg tgc tat tat ctg ggg gcc acc aca gat gca gcc acc aag atc cta    288
Leu Cys Tyr Tyr Leu Gly Ala Thr Thr Asp Ala Ala Thr Lys Ile Leu
                85                  90                  95 gga gaa gtc act cgt ccc atg agt gta cac ata cct gcc gtg aag att    336
Gly Glu Val Thr Arg Pro Met Ser Val His Ile Pro Ala Val Lys Ile
            100                 105                 110 tgt gag aag cta aag aag atg gac agc cag atc tgt gag ctg aaa tac    384
Cys Glu Lys Leu Lys Lys Met Asp Ser Gln Ile Cys Glu Leu Lys Tyr
        115                 120                 125 ggg aag aag ctg gac ttg gcg tcg gtg gac ctg tgg aag atg aga gtg    432
Gly Lys Lys Leu Asp Leu Ala Ser Val Asp Leu Trp Lys Met Arg Val
    130                 135                 140 gca gag cta aag cag atc ctt cag aga tgg ggg gaa gag tgc agg gca    480
Ala Glu Leu Lys Gln Ile Leu Gln Arg Trp Gly Glu Glu Cys Arg Ala
145                 150                 155                 160 tgt gcg gag aaa agt gac tac gtg aac ctc att aga gag ctg gcc ccc    528
Cys Ala Glu Lys Ser Asp Tyr Val Asn Leu Ile Arg Glu Leu Ala Pro
                165                 170                 175 aaa tat gta gag ata tac ccc caa acg gag ctc tga                    564
Lys Tyr Val Glu Ile Tyr Pro Gln Thr Glu Leu
            180                 185
```

```
<210> SEQ ID NO 4
<211> LENGTH: 187
<212> TYPE: PRT
<213> ORGANISM: Mus musculus

<400> SEQUENCE: 4
```

Met Arg Cys Ile Ser Pro Thr Ala Leu Val Thr Phe Cys Ala Gly Phe
 1               5                  10                  15

Cys Ile Ser Asn Pro Val Leu Ala Gln Gly Leu Glu Ala Gly Val Gly
                20                  25                  30

Pro Arg Ala Asp Cys Glu Val Cys Lys Glu Phe Leu Asp Arg Phe Tyr
            35                  40                  45

Asn Ser Leu Leu Ser Arg Gly Ile Asp Phe Ser Ala Asp Thr Ile Glu
        50                  55                  60

Lys Glu Leu Leu Asn Phe Cys Ser Asp Ala Lys Gly Lys Glu Asn Arg
65                  70                  75                  80

Leu Cys Tyr Tyr Leu Gly Ala Thr Thr Asp Ala Ala Thr Lys Ile Leu
                85                  90                  95

Gly Glu Val Thr Arg Pro Met Ser Val His Ile Pro Ala Val Lys Ile
                100                 105                 110

Cys Glu Lys Leu Lys Lys Met Asp Ser Gln Ile Cys Glu Leu Lys Tyr
            115                 120                 125

Gly Lys Lys Leu Asp Leu Ala Ser Val Asp Leu Trp Lys Met Arg Val
130                 135                 140

Ala Glu Leu Lys Gln Ile Leu Gln Arg Trp Gly Glu Glu Cys Arg Ala
145                 150                 155                 160

Cys Ala Glu Lys Ser Asp Tyr Val Asn Leu Ile Arg Glu Leu Ala Pro
                165                 170                 175

Lys Tyr Val Glu Ile Tyr Pro Gln Thr Glu Leu
            180                 185

```
<210> SEQ ID NO 5
<211> LENGTH: 26
<212> TYPE: DNA
<213> ORGANISM: Artificial Sequence
<220> FEATURE:
<223> OTHER INFORMATION: m-MANF2-ATG: primer used in cloning and
      expression analyses of mouse MANF2

<400> SEQUENCE: 5
accatgcggt gcatcagtcc aactgc                                          26

<210> SEQ ID NO 6
<211> LENGTH: 23
<212> TYPE: DNA
<213> ORGANISM: Artificial Sequence
<220> FEATURE:
<223> OTHER INFORMATION: m-MANF2-int-as: primer used in cloning and
      expression analyses of mouse MANF2

<400> SEQUENCE: 6
ctcatgggac gagtgacttc tcc                                             23

<210> SEQ ID NO 7
<211> LENGTH: 26
<212> TYPE: DNA
<213> ORGANISM: Artificial Sequence
<220> FEATURE:
<223> OTHER INFORMATION: m-MANF2-STOP: primer used in cloning and
      expression analyses of mouse MANF2

<400> SEQUENCE: 7
```

-continued gtcagagctc cgtttggggg tatatc                                              26

<210> SEQ ID NO 8
<211> LENGTH: 22
<212> TYPE: DNA
<213> ORGANISM: Artificial Sequence
<220> FEATURE:
<223> OTHER INFORMATION: m-MANF2-STOP-del: primer used in cloning and
      expression analyses of mouse MANF2

<400> SEQUENCE: 8
gagctccgtt tggggggtata tc                                                 22

<210> SEQ ID NO 9
<211> LENGTH: 26
<212> TYPE: DNA
<213> ORGANISM: Artificial Sequence
<220> FEATURE:
<223> OTHER INFORMATION: h-MANF2-ATG: primer used in cloning and
      expression analyses of human MANF2

<400> SEQUENCE: 9
accatgtggt gcgcgagccc agttgc                                              26

<210> SEQ ID NO 10
<211> LENGTH: 25
<212> TYPE: DNA
<213> ORGANISM: Artificial Sequence
<220> FEATURE:
<223> OTHER INFORMATION: h-MANF2-int-as: primer used in cloning and
      expression analyses of human MANF2

<400> SEQUENCE: 10
gcacactcat tgggcgagtg acttc                                               25

<210> SEQ ID NO 11
<211> LENGTH: 27
<212> TYPE: DNA
<213> ORGANISM: Artificial Sequence
<220> FEATURE:
<223> OTHER INFORMATION: h-MANF2-stop: primer used in cloning and
      expression analyses of human MANF2

<400> SEQUENCE: 11
gatcagagct ctgttttggg gtgtgtc                                             27

<210> SEQ ID NO 12
<211> LENGTH: 22
<212> TYPE: DNA
<213> ORGANISM: Artificial Sequence
<220> FEATURE:
<223> OTHER INFORMATION: h-MANF2-stop-del: primer used in cloning and
      expression analyses of human MANF2

<400> SEQUENCE: 12
gagctctgtt tggggtgtg tc                                                   22

<210> SEQ ID NO 13
<211> LENGTH: 179
<212> TYPE: PRT
<213> ORGANISM: Homo Sapiens

<400> SEQUENCE: 13

Met Trp Ala Thr Gln Gly Leu Ala Val Arg Val Ala Leu Ser Val Leu
 1               5                  10                  15

Pro Gly Ser Arg Ala Leu Arg Pro Gly Asp Cys Glu Val Cys Ile Ser
            20                  25                  30

Tyr Leu Gly Arg Phe Tyr Gln Asp Leu Lys Asp Arg Asp Val Thr Phe
        35                  40                  45

Ser Pro Ala Thr Ile Glu Asn Glu Leu Ile Lys Phe Cys Arg Glu Ala
    50                  55                  60

Arg Gly Lys Glu Asn Arg Leu Cys Tyr Tyr Ile Gly Ala Thr Asp Asp
65                  70                  75                  80

Ala Ala Thr Lys Ile Ile Asn Glu Val Ser Lys Pro Leu Ala His His
                85                  90                  95

Ile Pro Val Glu Lys Ile Cys Glu Lys Leu Lys Lys Lys Asp Ser Gln
            100                 105                 110

Ile Cys Glu Leu Lys Tyr Asp Lys Gln Ile Asp Leu Ser Thr Val Asp
        115                 120                 125

Leu Lys Lys Leu Arg Val Lys Glu Leu Lys Lys Ile Leu Asp Asp Trp
130                 135                 140

Gly Glu Thr Cys Lys Gly Cys Ala Glu Lys Ser Asp Tyr Ile Arg Lys
145                 150                 155                 160

Ile Asn Glu Leu Met Pro Lys Tyr Ala Pro Lys Ala Ala Ser Ala Pro
                165                 170                 175

Thr Asp Leu

<210> SEQ ID NO 14
<211> LENGTH: 153
<212> TYPE: PRT
<213> ORGANISM: Mus musculus

<400> SEQUENCE: 14

Cys Glu Val Cys Ile Ser Tyr Leu Gly Arg Phe Tyr Gln Asp Leu Lys
1               5                   10                  15

Asp Arg Asp Val Thr Phe Ser Pro Ala Thr Ile Glu Glu Leu Ile
            20                  25                  30

Lys Phe Cys Arg Glu Ala Arg Gly Lys Glu Asn Arg Leu Cys Tyr Tyr
        35                  40                  45

Ile Gly Ala Thr Asp Asp Ala Ala Thr Lys Ile Ile Asn Glu Val Ser
    50                  55                  60

Lys Pro Leu Ala His His Ile Pro Val Glu Lys Ile Cys Glu Lys Leu
65                  70                  75                  80

Lys Lys Lys Asp Ser Gln Ile Cys Glu Leu Lys Tyr Asp Lys Gln Ile
                85                  90                  95

Asp Leu Ser Thr Val Asp Leu Lys Lys Leu Arg Val Lys Glu Leu Lys
            100                 105                 110

Lys Ile Leu Asp Asp Trp Gly Glu Met Cys Lys Gly Cys Ala Glu Lys
        115                 120                 125

Ser Asp Tyr Ile Arg Lys Ile Asn Glu Leu Met Pro Lys Tyr Ala Pro
    130                 135                 140

Lys Ala Ala Ser Ala Arg Thr Asp Leu
145                 150

<210> SEQ ID NO 15
<211> LENGTH: 153
<212> TYPE: PRT
<213> ORGANISM: Rattus norvegivus

<400> SEQUENCE: 15

Cys Glu Val Cys Ile Ser Tyr Leu Gly Arg Phe Tyr Gln Asp Leu Lys

```
              1               5                  10                 15
        Asp Arg Asp Val Thr Phe Ser Pro Ala Thr Ile Glu Glu Leu Ile
                         20                  25                 30

Lys Phe Cys Arg Glu Ala Arg Gly Lys Glu Asn Arg Leu Cys Tyr Tyr
                         35                  40                 45

Ile Gly Ala Thr Asp Ala Ala Thr Lys Ile Ile Asn Glu Val Ser
         50                  55                  60

Lys Pro Leu Ala His His Ile Pro Val Glu Lys Ile Cys Glu Lys Leu
         65                  70                  75                 80

Lys Lys Lys Asp Ser Gln Ile Cys Glu Leu Lys Tyr Asp Lys Gln Ile
                         85                  90                 95

Asp Leu Ser Thr Val Asp Leu Lys Lys Leu Arg Val Lys Glu Leu Lys
                        100                 105                110

Lys Ile Leu Asp Asp Trp Gly Glu Met Cys Lys Gly Cys Ala Glu Lys
                        115                 120                125

Ser Asp Tyr Ile Arg Lys Ile Asn Glu Leu Met Pro Lys Tyr Ala Pro
                        130                 135                 140

Lys Ala Ala Ser Ala Arg Thr Asp Leu
        145                 150

<210> SEQ ID NO 16
<211> LENGTH: 153
<212> TYPE: PRT
<213> ORGANISM: Bos Taurus

<400> SEQUENCE: 16

Cys Glu Val Cys Ile Ser Tyr Leu Gly Arg Phe Tyr Gln Asp Leu Lys
         1               5                  10                 15

Asp Arg Asp Val Thr Phe Ser Pro Ala Ser Ile Glu Lys Glu Leu Ile
                         20                  25                 30

Lys Phe Cys Arg Glu Ala Arg Gly Lys Glu Asn Arg Leu Cys Tyr Tyr
                         35                  40                 45

Ile Gly Ala Thr Glu Asp Ala Ala Thr Lys Ile Ile Asn Glu Val Ser
         50                  55                  60

Lys Pro Leu Ser His His Ile Pro Val Glu Lys Ile Cys Glu Lys Leu
         65                  70                  75                 80

Lys Lys Lys Asp Ser Gln Ile Cys Glu Leu Lys Tyr Asp Lys Gln Ile
                         85                  90                 95

Asp Leu Ser Thr Val Asp Leu Lys Lys Leu Arg Val Lys Glu Leu Lys
                        100                 105                110

Lys Ile Leu Asp Asp Trp Gly Glu Thr Cys Lys Gly Cys Ala Glu Lys
                        115                 120                125

Ser Asp Tyr Ile Arg Lys Ile Asn Glu Leu Met Pro Lys Tyr Ala Pro
                        130                 135                 140

Lys Ala Ala Ser Ser Arg Thr Asp Leu
        145                 150

<210> SEQ ID NO 17
<211> LENGTH: 153
<212> TYPE: PRT
<213> ORGANISM: Gallus gallus
<220> FEATURE:
<221> NAME/KEY: misc_feature
<222> LOCATION: (123)..(124)
<223> OTHER INFORMATION: Xaa can be any naturally occurring amino acid

<400> SEQUENCE: 17
```

```
Cys Glu Val Cys Val Thr Phe Leu Gly Arg Phe Tyr Gln Ser Leu Lys
  1               5                  10                  15

Asp Asn Asn Val Glu Phe Thr Pro Ala Ser Ile Glu Lys Glu Leu Met
             20                  25                  30

Lys Ser Cys Arg Glu Ala Lys Gly Lys Glu Asn Arg Leu Cys Tyr Tyr
         35                  40                  45

Ile Gly Ala Thr Ser Asp Ala Ala Thr Lys Ile Ile Asn Glu Val Ser
     50                  55                  60

Lys Pro Met Ser His His Ile Pro Val Glu Lys Ile Cys Glu Lys Leu
 65                  70                  75                  80

Lys Lys Lys Asp Ser Gln Ile Cys Glu Leu Lys Tyr Asp Lys Gln Ile
                 85                  90                  95

Asp Leu Ser Thr Ala Asp Leu Arg Lys Leu Arg Val Lys Glu Leu Arg
            100                 105                 110

Arg Ile Leu Asp Asp Trp Gly Glu Ala Cys Xaa Xaa Cys Ala Glu Lys
            115                 120                 125

Ser Asp Phe Ile Arg Arg Ile His Glu Leu Met Pro Lys Tyr Ala Pro
            130                 135                 140

Arg Ala Ala Gly Ala Arg Ala Asp Leu
145                 150
```

<210> SEQ ID NO 18
<211> LENGTH: 153
<212> TYPE: PRT
<213> ORGANISM: Xenopus laevis

<400> SEQUENCE: 18

```
Cys Glu Val Cys Val Ser Phe Leu Ser Arg Phe Tyr Gln Ser Leu Lys
  1               5                  10                  15

Glu Arg Gln Val Glu Phe Lys Pro Asp Ala Val Glu Lys Glu Leu Leu
             20                  25                  30

Lys Thr Cys Asn Asp Ala Arg Gly Lys Glu Asn Arg Leu Cys Tyr Tyr
         35                  40                  45

Ile Gly Ala Thr Ser Asp Ala Ala Thr Lys Ile Thr Asn Glu Val Ser
     50                  55                  60

Lys Pro Leu Ser His His Ile Pro Ala Glu Lys Ile Cys Glu Lys Leu
 65                  70                  75                  80

Lys Lys Lys Asp Gly Gln Ile Cys Glu Leu Lys Tyr Asp Lys Gln Ile
                 85                  90                  95

Asp Leu Ser Thr Val Asp Leu Lys Lys Leu Lys Val Lys Glu Leu Lys
            100                 105                 110

Lys Ile Leu Asp Asp Trp Gly Glu Ser Cys Lys Gly Cys Ala Glu Lys
            115                 120                 125

Ser Asp Phe Ile Arg Lys Ile Asn Glu Leu Met Pro Lys Tyr Ala Pro
            130                 135                 140

His Ala Ala Asn Ala Arg Thr Asp Leu
145                 150
```

<210> SEQ ID NO 19
<211> LENGTH: 153
<212> TYPE: PRT
<213> ORGANISM: Fugu rubribes

<400> SEQUENCE: 19

```
Cys Pro Val Cys Ile Ala Phe Leu Gly Arg Phe Tyr Asp Ser Leu Lys
  1               5                  10                  15
```

```
Asp Asn Glu Val Ala Phe Asn Val Asp Ile Glu Lys Ala Leu Thr
                20                  25                  30

Lys Ser Cys Asn Asp Ala Lys Gly Lys Glu Asn Arg Gln Cys Tyr Tyr
            35                  40                  45

Ile Gly Ala Thr Ser Asp Ala Ala Thr Lys Met Ile Asn Glu Val Ser
 50                  55                  60

Lys Pro Met Ser His His Val Pro Val Glu Lys Ile Cys Glu Lys Leu
 65                  70                  75                  80

Lys Lys Lys Asp Ser Gln Ile Cys Glu Leu Lys Tyr Asp Lys Gln Leu
                85                  90                  95

Asp Leu Ser Thr Val Asp Leu Lys Lys Leu Lys Val Lys Asp Leu Lys
            100                 105                 110

Lys Val Leu Glu Asp Trp Gly Glu Ser Cys Lys Gly Cys Ala Glu Lys
        115                 120                 125

Ser Asp Phe Ile Arg Lys Ile Thr Glu Leu Met Pro Lys Tyr Ala Pro
130                 135                 140

Ala Ala Ala Arg Ala Arg Thr Glu Leu
145                 150

<210> SEQ ID NO 20
<211> LENGTH: 153
<212> TYPE: PRT
<213> ORGANISM: Danio rerio

<400> SEQUENCE: 20

Cys Glu Val Cys Val Gly Phe Leu Gln Arg Leu Tyr Gln Thr Ile Gln
 1               5                  10                  15

Glu Asn Asn Val Lys Phe Asp Ser Asp Ser Ile Glu Lys Ala Leu Leu
                20                  25                  30

Lys Ser Cys Lys Asp Ala Lys Gly Lys Glu Asn Arg Phe Cys Tyr Tyr
            35                  40                  45

Ile Gly Ala Thr Ser Asp Ala Ala Thr Lys Ile Thr Asn Glu Val Ser
 50                  55                  60

Lys Pro Met Ser Tyr His Val Pro Val Glu Lys Ile Cys Glu Lys Leu
 65                  70                  75                  80

Lys Lys Lys Asp Ser Gln Ile Cys Glu Leu Lys Tyr Asp Lys Gln Val
                85                  90                  95

Asp Leu Ser Val Asp Leu Lys Leu Lys Val Lys Asp Leu Lys
            100                 105                 110

Lys Ile Leu Glu Glu Trp Gly Glu Ser Cys Lys Gly Cys Val Glu Lys
        115                 120                 125

Ser Asp Phe Ile Arg Lys Ile Asn Glu Leu Met Pro Lys Tyr Ala Pro
130                 135                 140

Ser Ala Ala Lys Ala Arg Thr Asp Leu
145                 150

<210> SEQ ID NO 21
<211> LENGTH: 146
<212> TYPE: PRT
<213> ORGANISM: Drosophila melanogaster

<400> SEQUENCE: 21

Cys Glu Val Cys Val Lys Thr Val Arg Arg Phe Ala Asp Ser Leu Asp
 1               5                  10                  15

Asp Ser Thr Lys Lys Asp Tyr Lys Gln Ile Glu Thr Ala Phe Lys Lys
                20                  25                  30
```

```
Phe Cys Lys Ala Gln Lys Asn Lys Glu His Arg Phe Cys Tyr Tyr Leu
        35                  40                  45

Gly Gly Leu Glu Glu Ser Ala Thr Gly Ile Leu Asn Glu Leu Ser Lys
    50                  55                  60

Pro Leu Ser Trp Ser Met Pro Ala Glu Lys Ile Cys Glu Lys Leu Lys
65                  70                  75                  80

Lys Lys Asp Ala Gln Ile Cys Asp Leu Arg Tyr Glu Lys Gln Ile Asp
            85                  90                  95

Leu Asn Ser Val Asp Leu Lys Lys Leu Lys Val Arg Asp Leu Lys Lys
                100                 105                 110

Ile Leu Asn Asp Trp Asp Glu Ser Cys Asp Gly Cys Leu Glu Lys Gly
        115                 120                 125

Asp Phe Ile Lys Arg Ile Glu Glu Leu Lys Pro Lys Tyr Ser Arg Ser
    130                 135                 140

Glu Leu
145

<210> SEQ ID NO 22
<211> LENGTH: 147
<212> TYPE: PRT
<213> ORGANISM: Canorhabditis elegans

<400> SEQUENCE: 22

Cys Glu Val Cys Lys Lys Val Leu Asp Asp Val Met Ala Lys Val Pro
1               5                   10                  15

Ala Gly Asp Lys Ser Lys Pro Asp Ala Ile Gly Lys Val Ile Arg Glu
            20                  25                  30

His Cys Glu Thr Thr Arg Asn Lys Glu Asn Lys Phe Cys Phe Tyr Ile
        35                  40                  45

Gly Ala Leu Pro Glu Ser Ala Thr Ser Ile Met Asn Glu Val Thr Lys
    50                  55                  60

Pro Leu Ser Trp Ser Met Pro Thr Glu Lys Val Cys Leu Glu Lys Leu
65                  70                  75                  80

Lys Gly Lys Asp Ala Gln Ile Cys Glu Leu Lys Tyr Asp Lys Pro Leu
            85                  90                  95

Asp Trp Lys Thr Ile Asp Leu Lys Lys Met Arg Val Lys Glu Leu Lys
                100                 105                 110

Asn Ile Leu Gly Glu Trp Gly Glu Val Cys Lys Gly Cys Thr Glu Lys
        115                 120                 125

Ala Glu Leu Ile Lys Arg Ile Glu Glu Leu Lys Pro Lys Tyr Val Lys
    130                 135                 140

Glu Glu Leu
145
```